(12) United States Patent
Pereira et al.

(10) Patent No.: US 10,246,735 B2
(45) Date of Patent: Apr. 2, 2019

(54) METHODS FOR PREPARING SAMPLES FOR NUCLEIC ACID AMPLIFICATION

(71) Applicant: LUMORA LTD., Cambridge, Cambridgeshire (GB)

(72) Inventors: Clint Pereira, Cambridge (GB); Cathal Joseph McElgunn, Cambridge (GB); Laurence Carlo Tisi, Cambridge (GB)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 495 days.

(21) Appl. No.: 14/389,526

(22) PCT Filed: Mar. 28, 2013

(86) PCT No.: PCT/GB2013/050846
§ 371 (c)(1),
(2) Date: Sep. 30, 2014

(87) PCT Pub. No.: WO2013/144654
PCT Pub. Date: Oct. 3, 2013

(65) Prior Publication Data
US 2015/0080562 A1    Mar. 19, 2015

(30) Foreign Application Priority Data

Mar. 30, 2012   (GB) .................................... 1205769.1

(51) Int. Cl.
| | | |
|---|---|---|
| *C12Q 1/68* | (2018.01) | |
| *C12N 15/10* | (2006.01) | |
| *C12Q 1/6806* | (2018.01) | |
| *B01D 15/16* | (2006.01) | |

(Continued)

(52) U.S. Cl.
CPC ......... *C12Q 1/6806* (2013.01); *B01D 15/161* (2013.01); *B01D 15/3876* (2013.01); *B01L 3/502* (2013.01); *C12N 15/101* (2013.01); *C12N 15/1006* (2013.01); *B01L 2300/0681* (2013.01); *B01L 2300/0832* (2013.01); *B01L 2400/0442* (2013.01)

(58) Field of Classification Search
CPC .......................... C12Q 1/6806; C12N 15/1006
USPC ........................................... 435/6.1; 422/68.1
See application file for complete search history.

(56) References Cited

U.S. PATENT DOCUMENTS

| | | |
|---|---|---|
| 555,500 A | 3/1896 | Denk |
| 1,994,323 A | 3/1935 | Peirce |
| 6,465,640 B1 | 10/2002 | Hood |

(Continued)

FOREIGN PATENT DOCUMENTS

| | | |
|---|---|---|
| CN | 101287449 A | 10/2008 |
| DE | 10 2007 021952 | 11/2007 |

(Continued)

OTHER PUBLICATIONS

Premstaller et al, "Temperature-modulated array high-performance liquid chromatography"; Genome Research, Nov. 2011; 11(11):1944-1951.

(Continued)

*Primary Examiner* — Jezia Riley
(74) *Attorney, Agent, or Firm* — Nixon & Vanderhye P.C.

(57) ABSTRACT

The present invention is in the field of sample preparation. In particular, it relates to methods for preparing samples prior to performing nucleic acid amplification.

18 Claims, 25 Drawing Sheets

(51) Int. Cl.
    B01D 15/38    (2006.01)
    B01L 3/00     (2006.01)

(56) References Cited

U.S. PATENT DOCUMENTS

| | | | |
|---|---|---|---|
| 7,811,758 | B2 | 10/2010 | Mori et al. |
| 2003/0129614 | A1 | 7/2003 | Parameswaran et al. |
| 2004/0126783 | A1 | 7/2004 | Bortolin et al. |
| 2004/0208792 | A1* | 10/2004 | Linton .......... B01L 3/5025 422/552 |
| 2005/0095626 | A1 | 5/2005 | Komazawa et al. |
| 2007/0269829 | A1 | 11/2007 | Yamashita et al. |
| 2008/0131949 | A1 | 6/2008 | Bortolin et al. |
| 2008/0275228 | A1 | 11/2008 | Mori et al. |
| 2009/0023904 | A1 | 1/2009 | Shoji et al. |

FOREIGN PATENT DOCUMENTS

| | | |
|---|---|---|
| EP | 1 512 741 | 3/2005 |
| EP | 2 017 339 | 1/2009 |
| JP | H07-509653 A | 10/1995 |
| JP | 2002-515508 A | 5/2002 |
| JP | 2005-095003 A | 4/2005 |
| JP | 2005-278438 A | 10/2005 |
| JP | 2005-532072 | 10/2005 |
| JP | 2007-306867 A | 11/2007 |
| JP | 2009-022187 A | 2/2009 |
| WO | WO 94/03250 | 2/1994 |
| WO | 99/60005 | 11/1999 |
| WO | 03/033740 | 4/2003 |
| WO | WO 2003/033740 | 4/2003 |
| WO | WO 03/087335 | 10/2003 |
| WO | 2004/005553 | 1/2004 |
| WO | 2005/093053 | 10/2005 |
| WO | 2011/124705 | 10/2011 |

OTHER PUBLICATIONS

Great Britain Search Report issued for Application No. GB1205769.1, dated Jul. 25, 2012.
Kleparnik, et al. "The use of elevated column temperature to extend DNA sequencing read lengths in capillary electrophoresis with replaceable polymer matrices" Electrophoresis. Dec. 1996; 17 (12):1860-6.
International Search Report dated Jul. 3, 2013, issued in connection with PCT/GB2013/050846.
International Search Report for PCT/GB2013/050846 dated Jul. 3, 2013.
Written Opinion of the International Searching Authority for PCT/GB2013/050846 dated Jul. 3, 2013.
English translation of Japanese Office Action dated Feb. 14, 2017, issued in connection with Japanese Patent Application No. 2015-502459 ("Methods for Preparing Samples for Nucleic Acid Amplification" Lumora Ltd.).
Japanese Office Action dated Feb. 14, 2017, issued in connection with Japanese Patent Application No. 2015-502459 ("Methods for Preparing Samples for Nucleic Acid Amplification" Lumora Ltd.).
Official Action Summary dated Feb. 14, 2017, issued in connection with Japanese Patent Application No. 2015-502459 ("Methods for Preparing Samples for Nucleic Acid Amplification" Lumora Ltd.).
English translation of Notification of Third Office Action dated Feb. 7, 2017, issued in connection with Japaense Patent Application No. 201380028534.9 ("Methods for Preparing Samples for Nucleic Acid Amplification" Lumora Ltd.).
Japanese Notification of Third Office Action dated Feb. 7, 2017, issued in connection with Japaense Patent Application No. 201380028534.9 ("Methods for Preparing Samples for Nucleic Acid Amplification" Lumora Ltd.).
"The Vacuum Brewer" from an article entitled "A Trip Inside Your Coffee Pot", [retrieved Oct. 26, 2017] http://www.jitterbuzz.com/coftrip.html.
Nov. 7, 2017 Communication of a Notice of Opposition of EP2831230 B1.
Gill et al., "Nucleic Acid Isothermal Amplification Technologies—A Review," Nucleosides, Nucleotides and Nucleic Acids, vol. 27, Issue 3, Mar. 2008, pp. 224-243.
Johnson, "Breaking Up Isn't Hard To Do: A cacophony of sonicators, cell bombs and grinders," The Scientist Magazine, Nov. 1998, 12(22):23.
Abu Al-Soud et al., "Capacity of Nine Thermostable DNA Polymerases To Mediate DNA Amplification in the Presence of PCR-Inhibiting Samples," Applied Environmental Microbiology, Oct. 1998, vol. 64, No. 10, pp. 3748-3753.
Walsh et al., "Chelex 100 as a Medium for Simple Extraction of DNA for PCR-Based Typing from Forensic Material," Biotechniques, Apr. 1991, pp. 134-139, 10(4):506-513.
Holben et al., "DNA Probe Method for the Detection of Specific Microorganisms in the Soil Bacterial Community," Applied Environmental Microbiology, Mar. 1988, vol. 54, No. 3, pp. 703-711.
Wallace, "Large and small scale phenol extractions," Methods in Enzymology, vol. 152, pp. 33-41, 1987.
Boom et al., "Rapid and Simple Method for Purification of Nucleic Acids," Journal of Clinical Microbiology, Mar. 1990, vol. 28, No. 3, pp. 495-503.
Odumeru et al., "*Salmonella* Detection Methods for Food and Food Ingredients," *Salmonella—A Dangerous Foodborne Pathogen*, Ed. Barakat S. M. Mahmoud, InTech, Rijeka, Croatia, 2012.
Berensmeier, "Magnetic particles for the separation and purification of nucleic acids," Applied Microbiology Biotechnology (2006), 73(3), pp. 495-504.
Notomi et al., "Loop-mediated isothermal amplification of DNA," Nucleic Acids Research, 2000, vol. 28, No. 12, E63.
Gandelman et al., "Novel Bioluminescent Quantitative Detection of Nucleic Acid Amplification in Real-Time," Public Library of Science, Nov. 2010, vol. 5, Issue 11, e14155.
Brown, "Purification of DNA from living cells," *Gene Cloning: An Introduction*. 3rd Ed. Chapman & Hall, 1995, pp. 27-35.
Maniatis, "Appendix A: Biochemical Techniques," *Molecular Cloning: A Laboratory Manual*, Cold Spring Harbor Laboratory, 1982, pp. 458-460.

\* cited by examiner

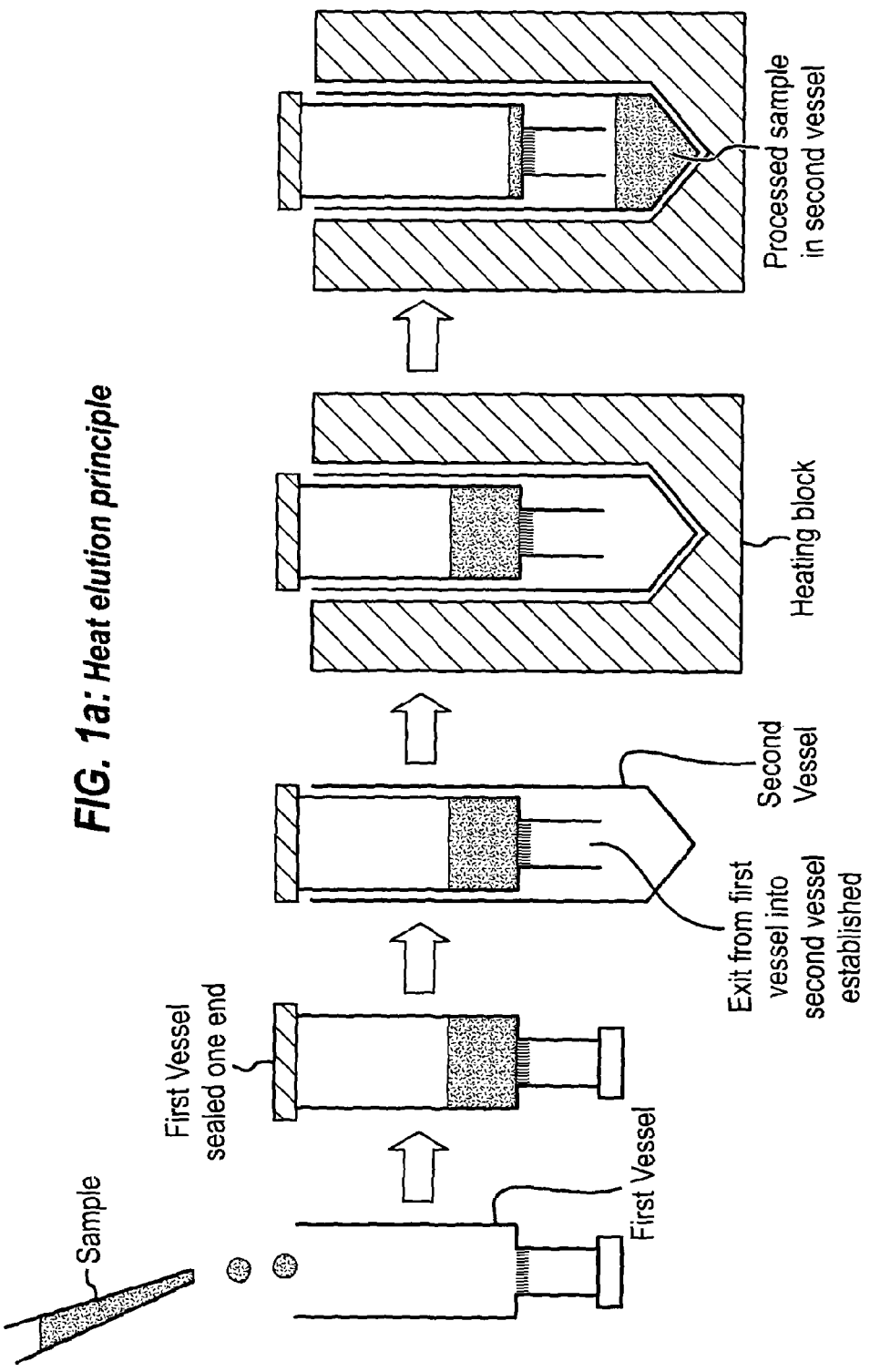

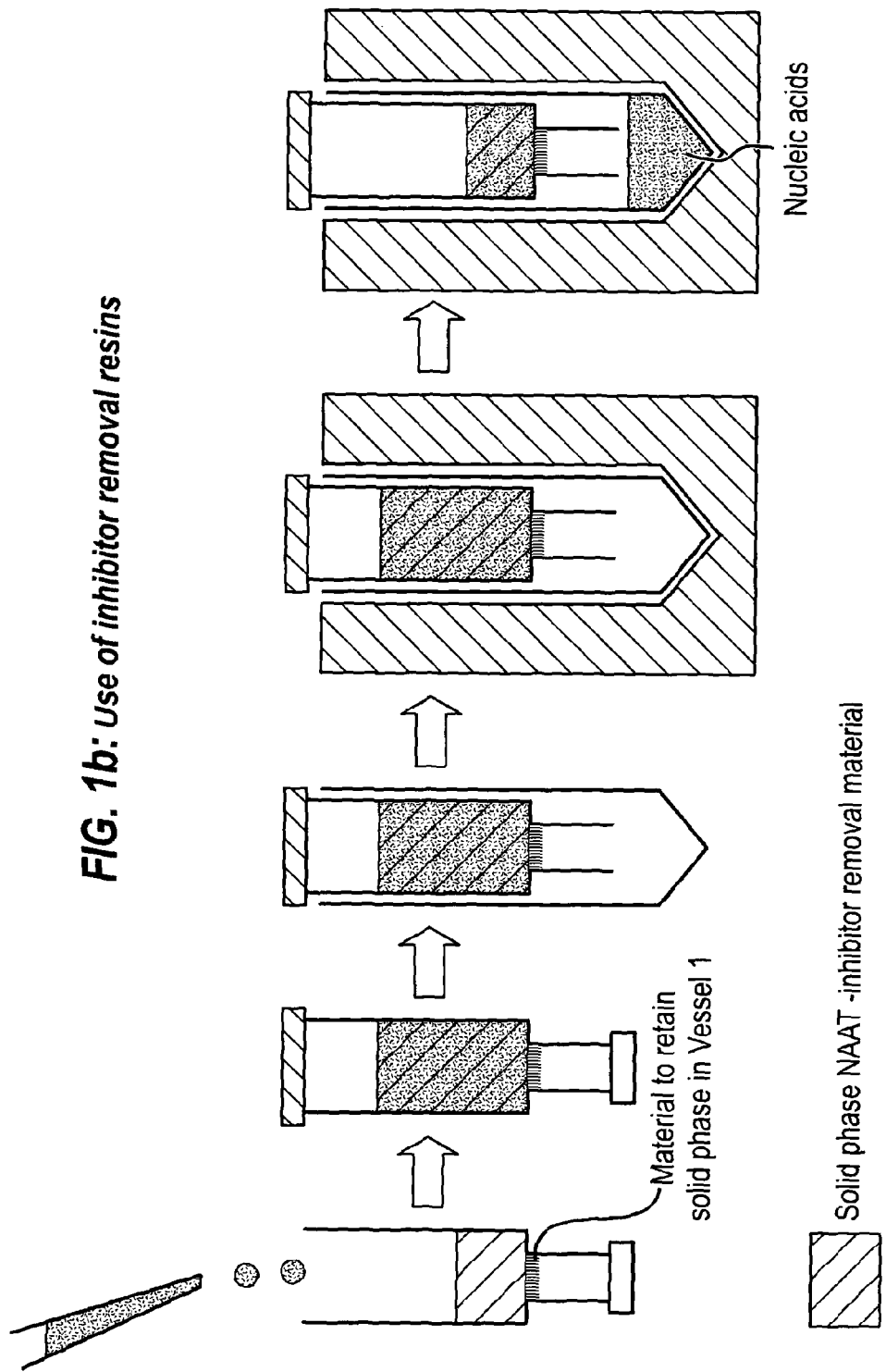

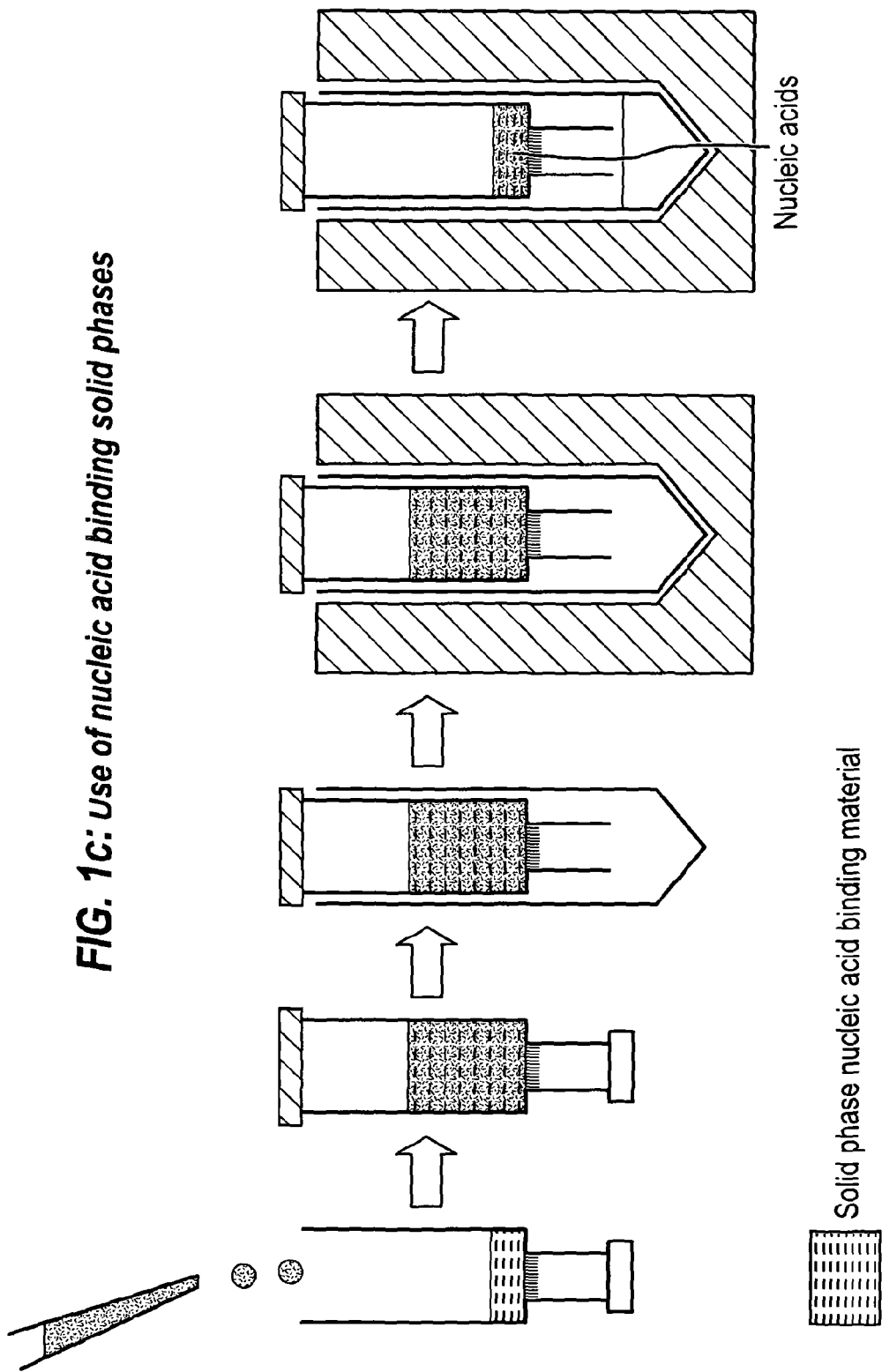
FIG. 1c: Use of nucleic acid binding solid phases

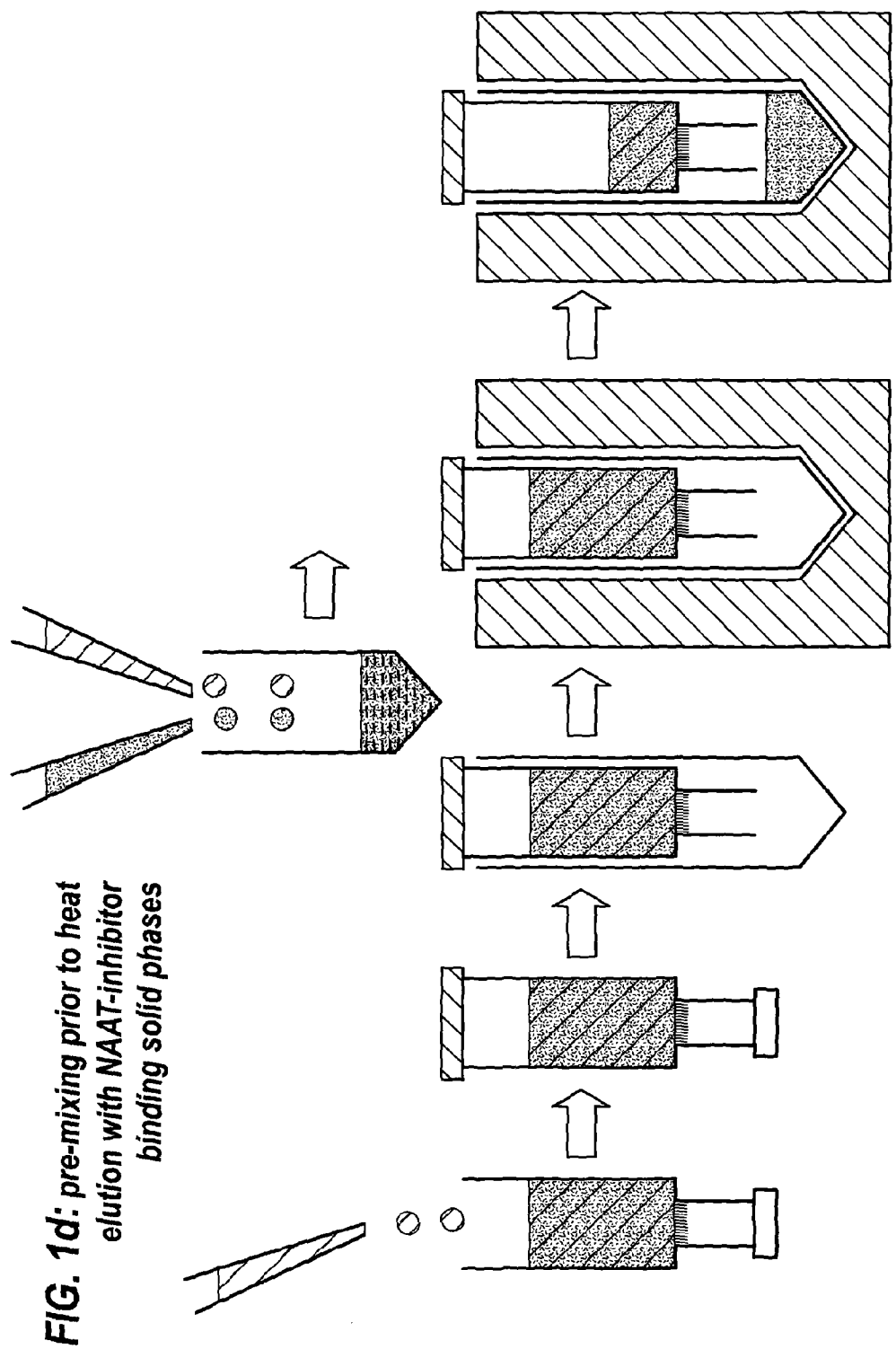
FIG. 1d: pre-mixing prior to heat elution with NAAT-inhibitor binding solid phases

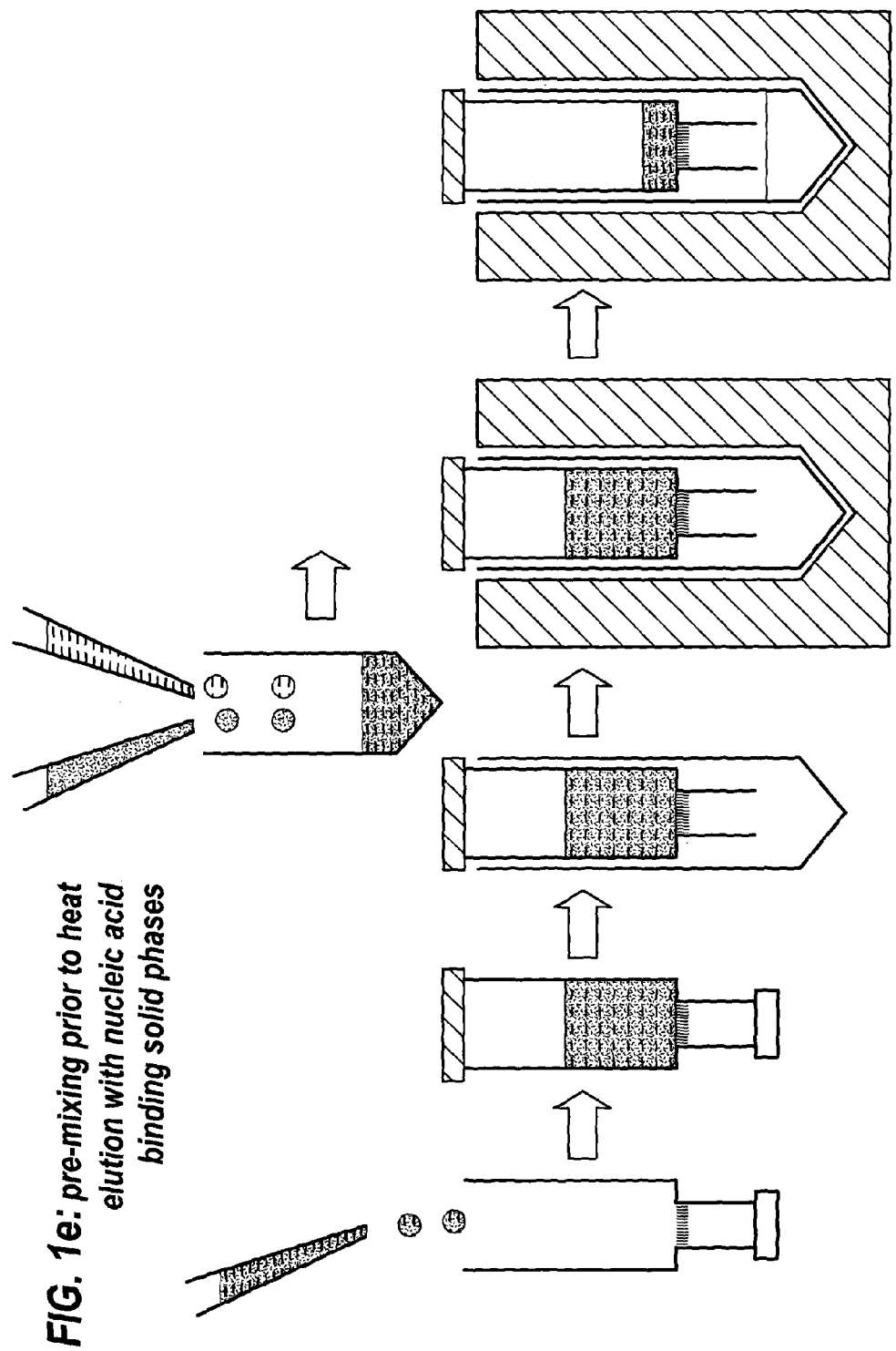
FIG. 1e: pre-mixing prior to heat elution with nucleic acid binding solid phases

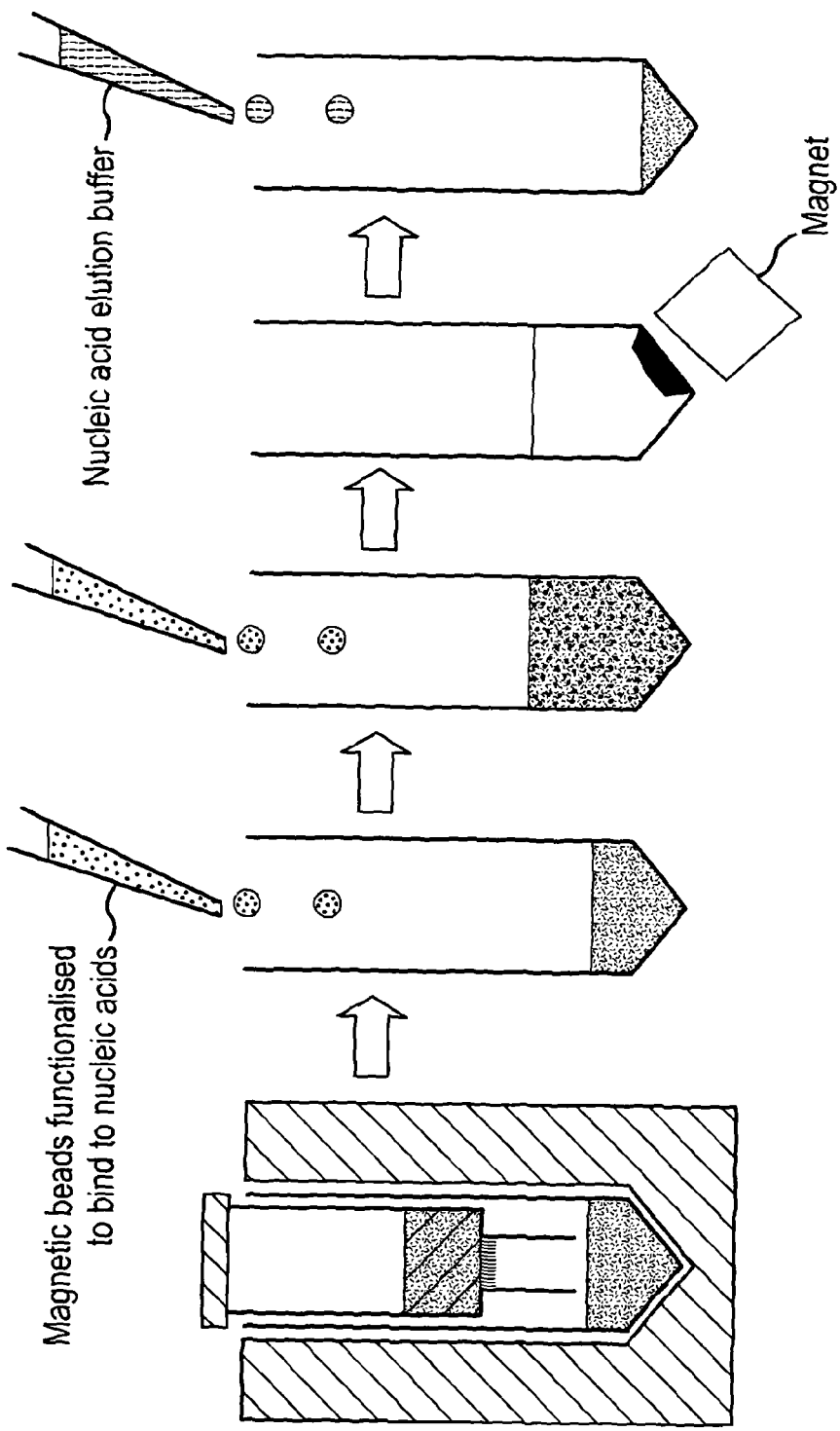
FIG. 1f: Post heat-elution concentration

FIG. 2

| # | Empty column (g) | Column with Chelex (g) | Weight of Chelex (g) | Collection tube (g) | MGW added | Treatment | Collection tube post-elution | Elution vol. (μl) | Post elution column weight (g) | Weight of MGW left on column (g) | Weight of column and collection tube | Combined pre MGW weight | Weight of MGW |
|---|---|---|---|---|---|---|---|---|---|---|---|---|---|
| 1 | 0.8695 | 0.9525 | 0.0830 | 1.2103 | 250μl | 100°C 5 mins | 1.4088 | 198.5 | 0.9991 | 0.0466 | | | |
| 2 | 0.8647 | 0.9498 | 0.0851 | 1.2029 | 250μl | RT 5 min | 1.2029 | 0 | 1.1957 | 0.2459 | | | |
| 3 | 0.8673 | | | 1.2101 | 250μl | 100°C 5 mins | 1.4365 | 226.4 | 0.8860 | 0.0187 | 2.3227 | 2.0774 | 0.2453 |
| 4 | 0.8682 | | | 1.2100 | 250μl | RT 5 min | 1.2100 | 0 | 0.1186 | 0.2504 | 2.3287 | 2.0782 | 0.2505 |

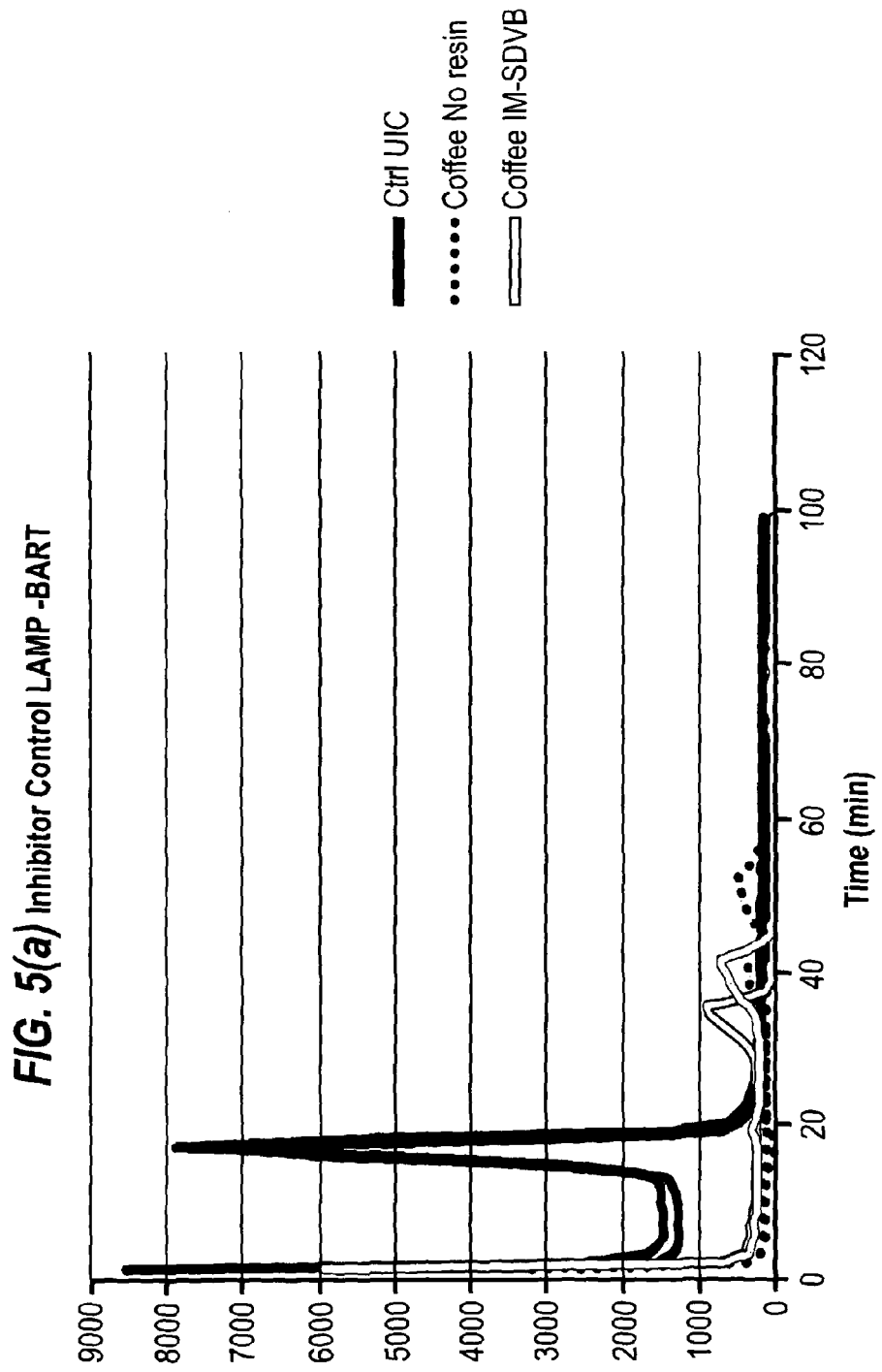

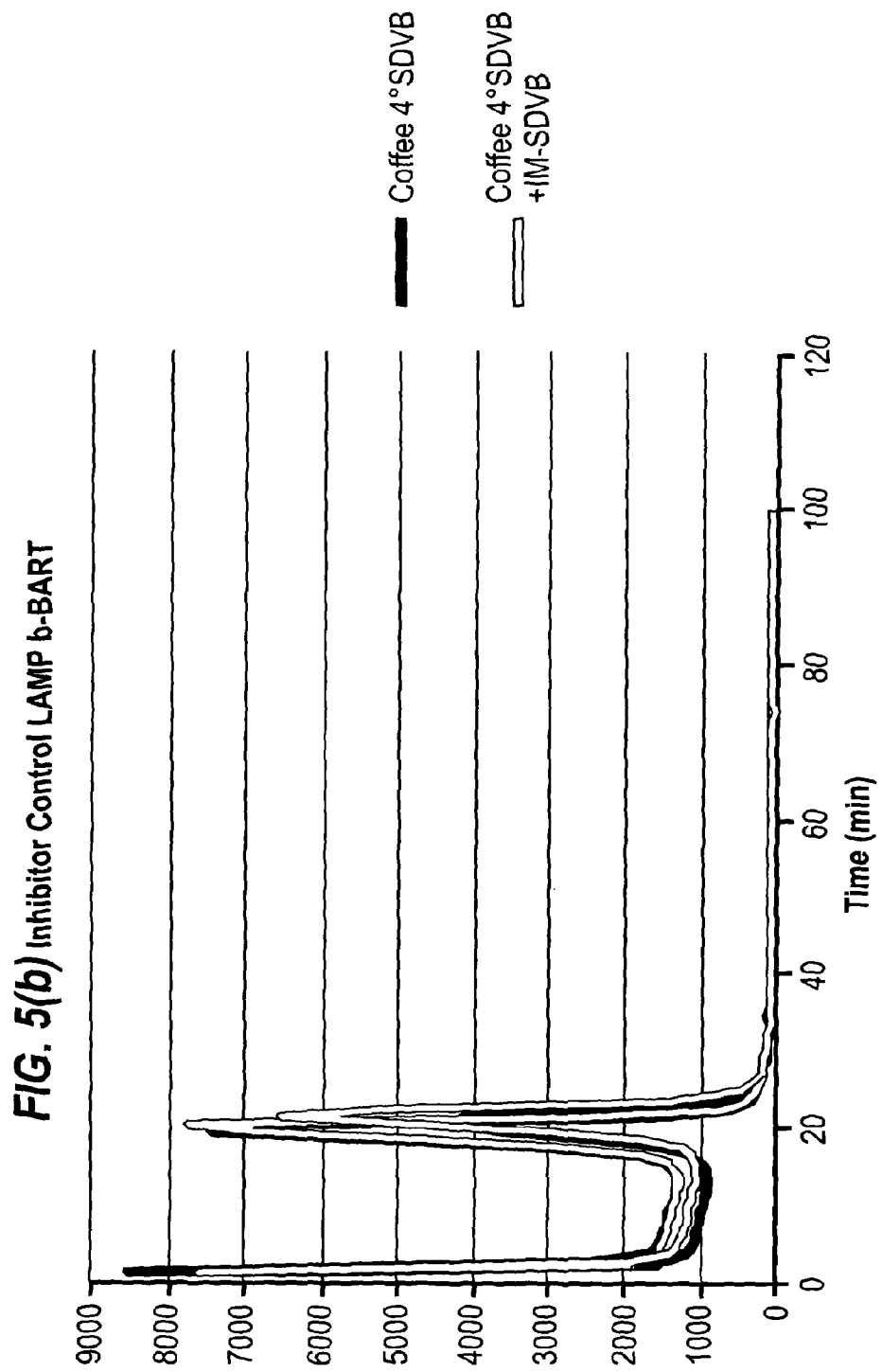
FIG. 5(b) Inhibitor Control LAMP b-BART

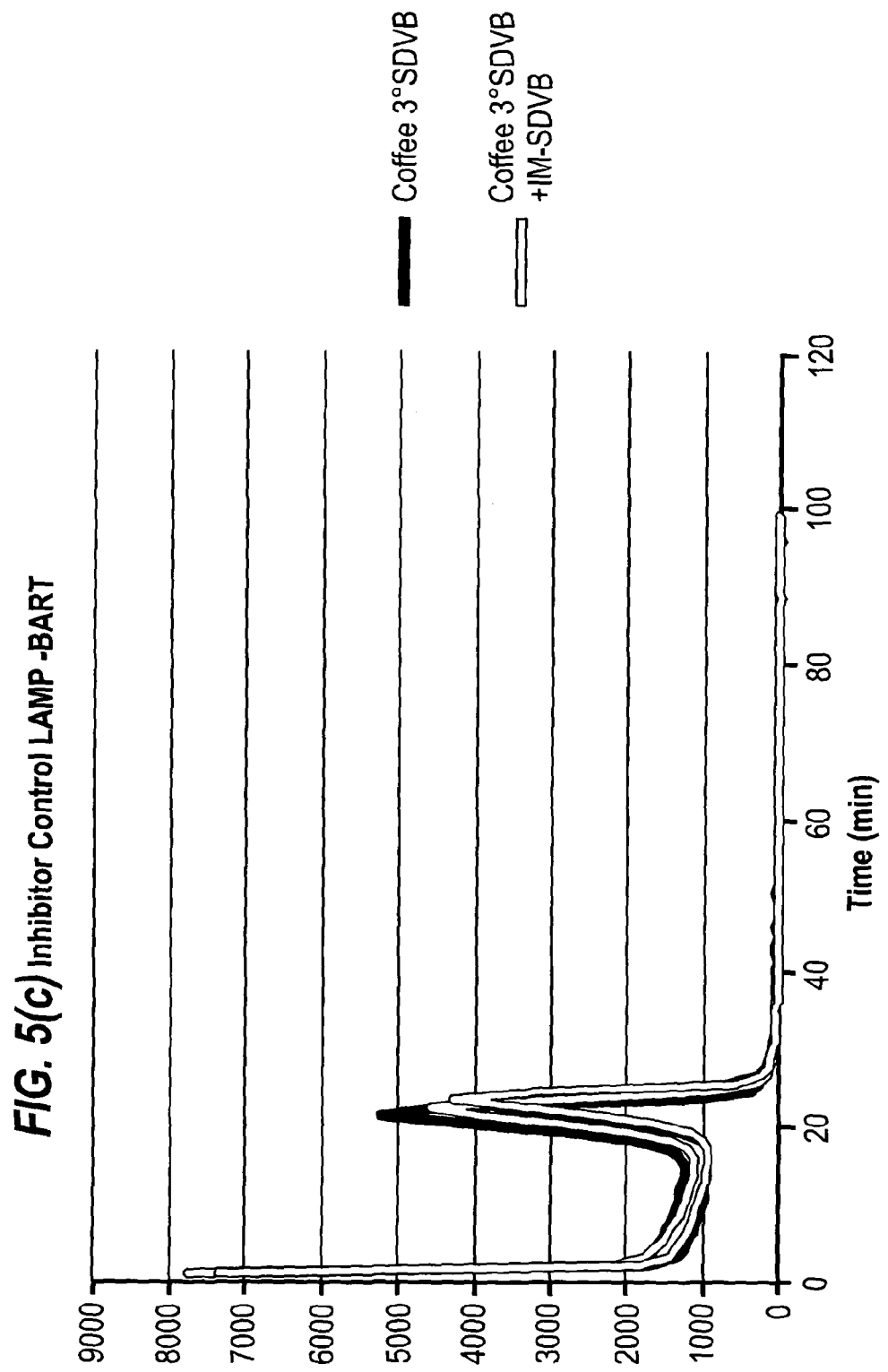

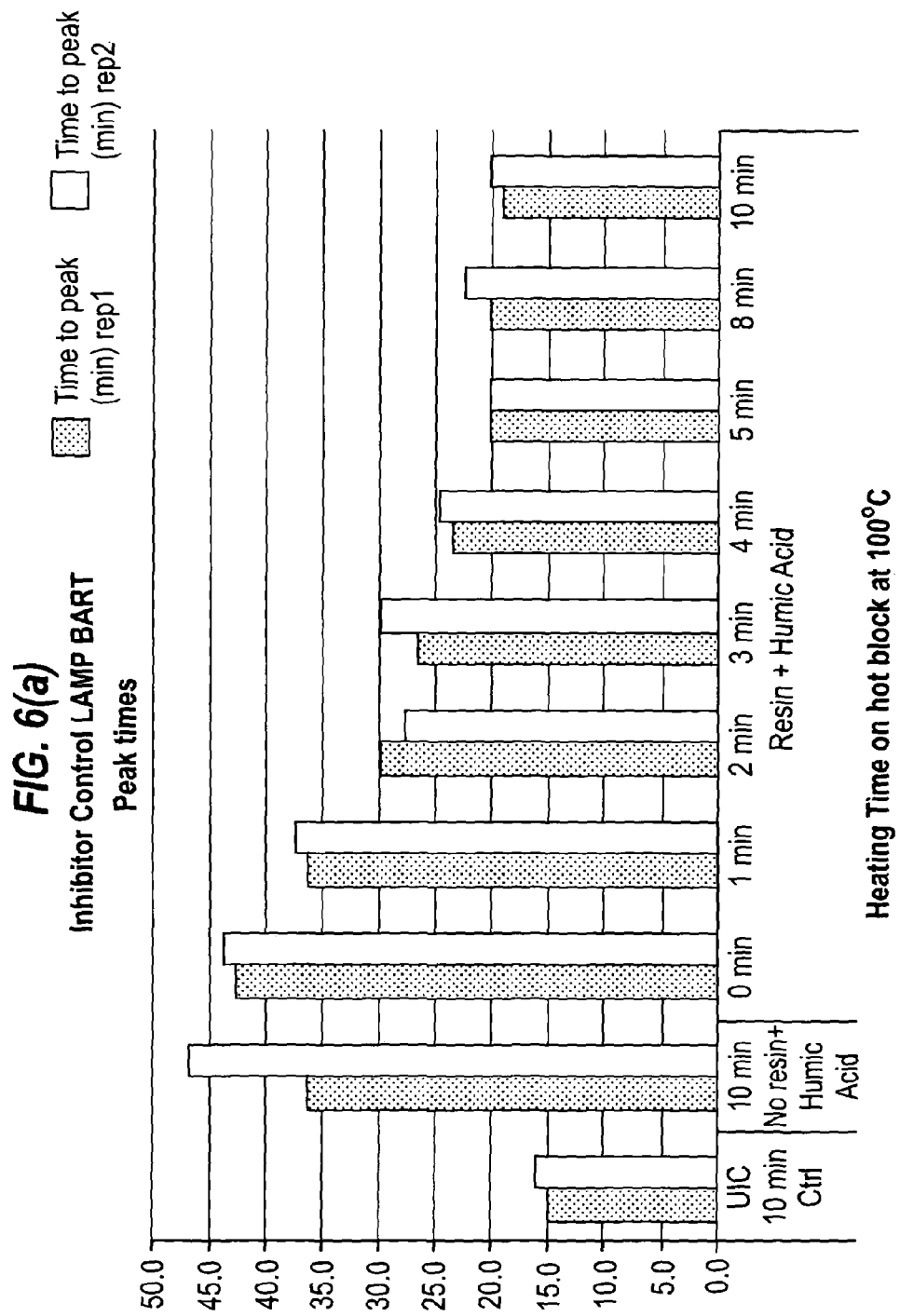

FIG. 9

| Format using 8 ml containers containing: | Time to elute (min) approx 1965 µl liquid |
|---|---|
| Resin mixture + polyethylene frit | 1.5 min |
| Resin mixture + 300mg paraffin wax* + polyethylene frit | 2 min (1 min delay before first drops then fast elution due to pressure build up) |
| SPC** frit + Resin mixture + polyethylene frit (Resin packed between frits) | 3 min |
| SPC frit + Resin mixture + 300mg paraffin wax* + polyethylene frit (resin packed between frits) | 3 min (1 min delay before first drops then fast elution due to pressure build up) |
| Resin mixture + 300mg paraffin wax* + SPC frit + polyethylene frit | 5 min (2 min 15 sec delay before first drops) |

*High melting temperature Paraffin wax (mp 70-80°)
**SPC =Ultra fine porous polyethylene sheet  SPC technologies # PE2030 14 µm pore size

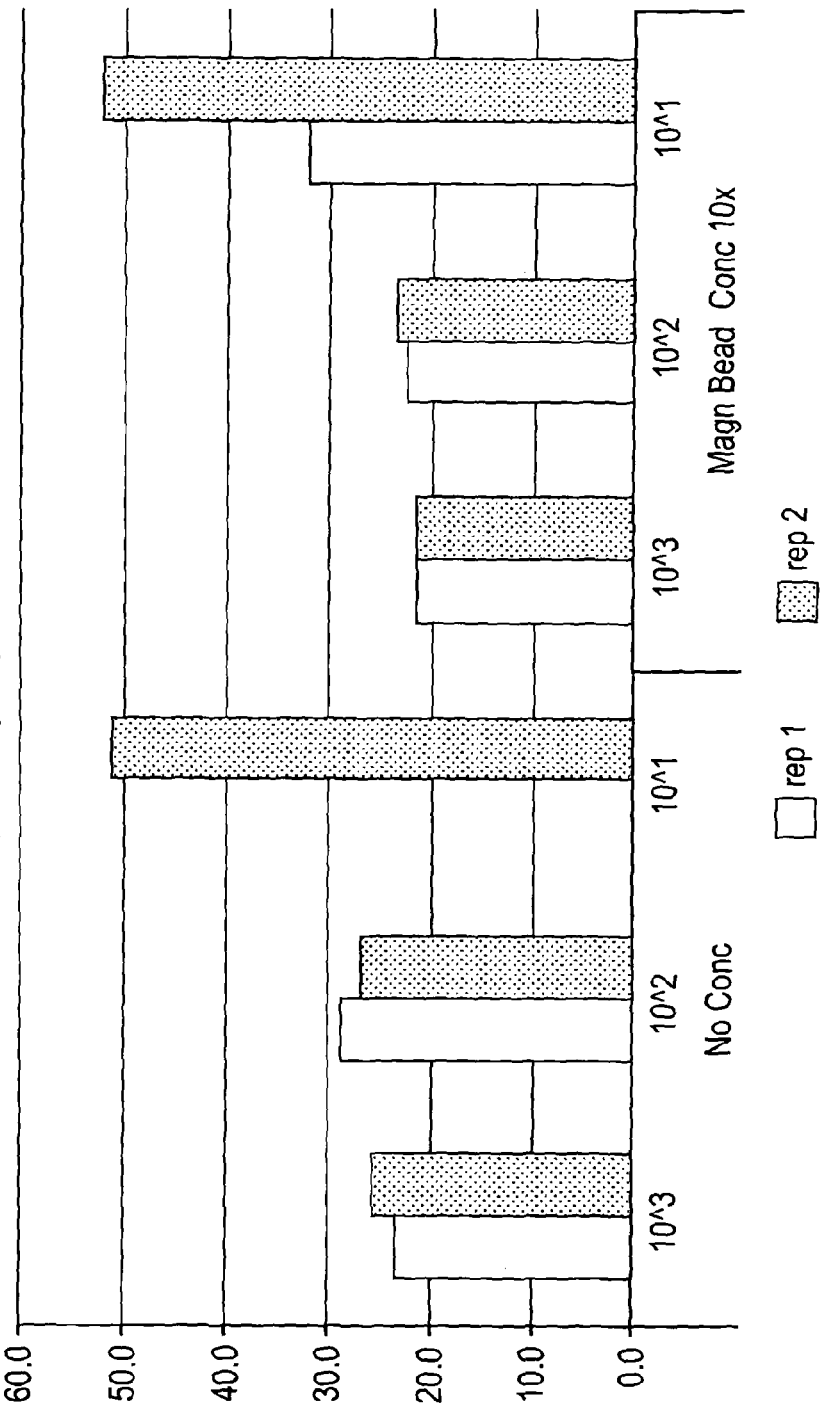

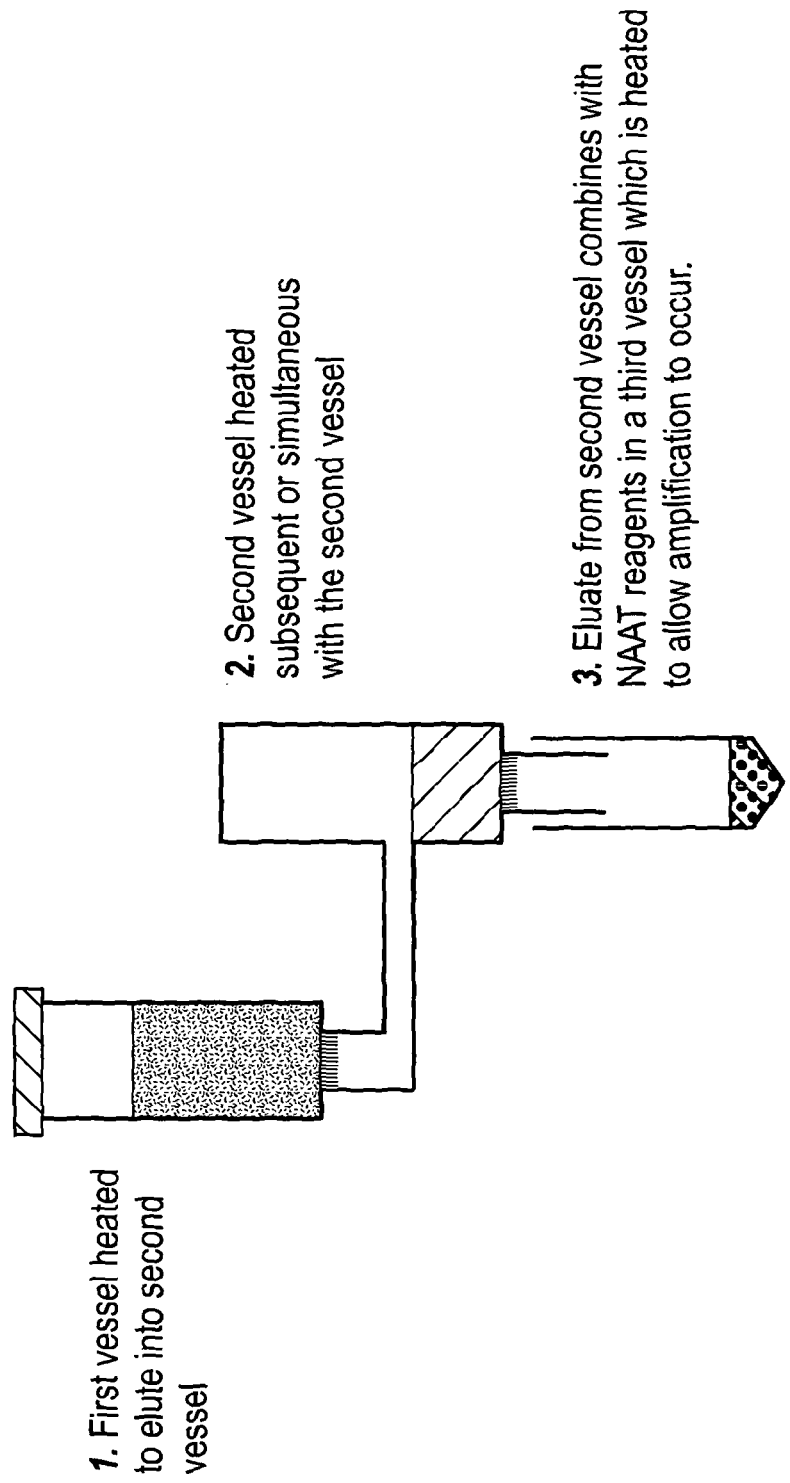

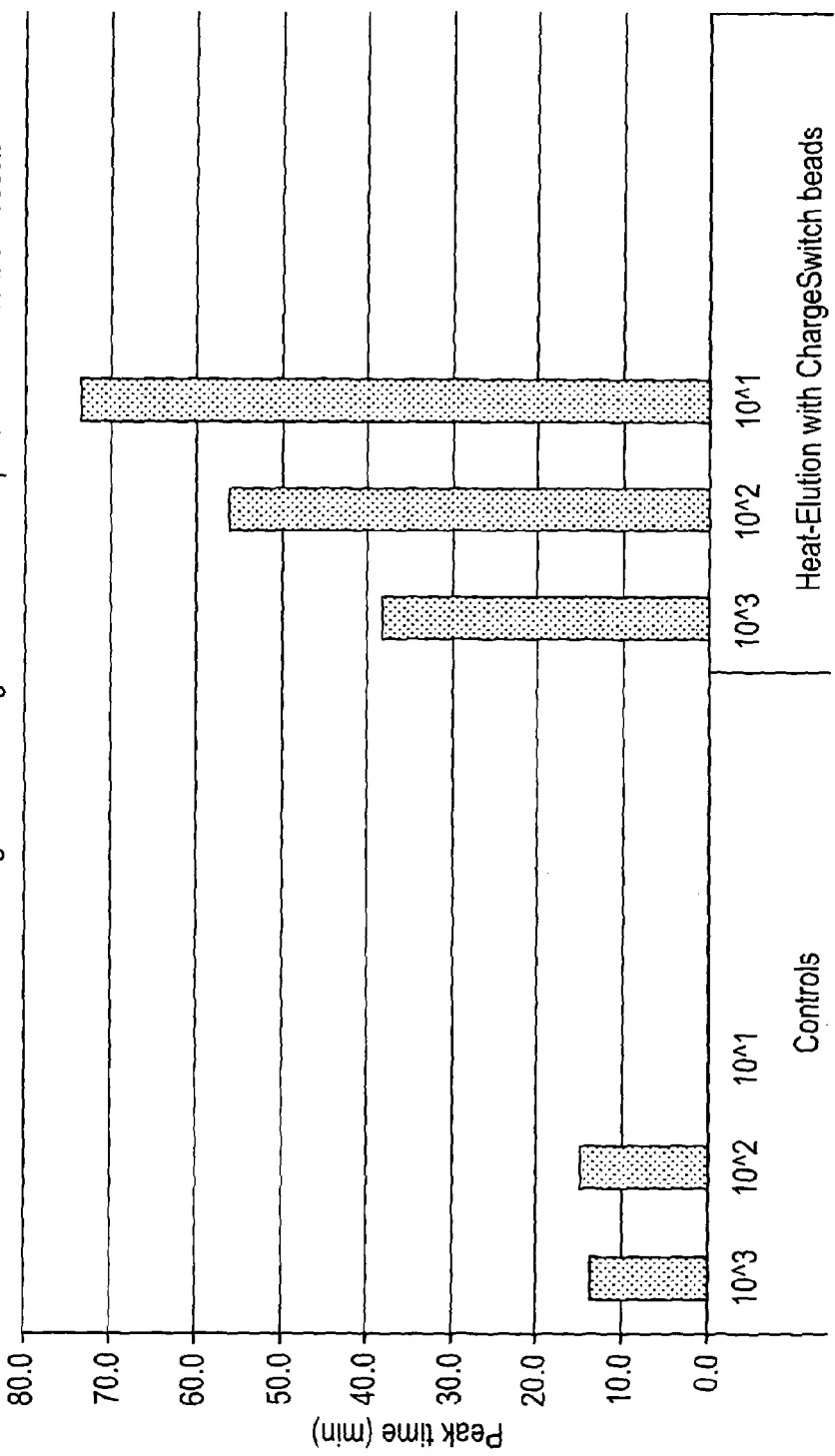
FIG. 16 Comparison of C. difficile genomic DNA detection with and without performing Heat-Elution with ChargeSwitch® magnetic beads incorporated into the first vessel.

METHODS FOR PREPARING SAMPLES FOR NUCLEIC ACID AMPLIFICATION

This application is the U.S. national phase of International Application No. PCT/GB2013/050846 filed 28 Mar. 2013 which designated the U.S. and claims priority to GB 1205769.1 filed 30 Mar. 2012, the entire contents of each of which are hereby incorporated by reference.

This application claims priority from GB1205769.1 filed on 30 Mar. 2012, the complete contents of which are incorporated by reference.

FIELD OF THE INVENTION

The present invention is in the field of sample preparation. In particular, it relates to methods for preparing samples prior to performing nucleic acid amplification.

BACKGROUND

Nucleic Acid Amplification Technologies, "NAATs"

NAATs allow the detection and quantification of a nucleic acid in a sample with high sensitivity and specificity. NAATs may be used to determine the presence of a particular template nucleic acid in a sample, as indicated by the presence of an amplification product following the implementation of a particular NAAT. Conversely, the absence of any amplification product indicates the absence of template nucleic acid in the sample. Such techniques are of great importance in clinical, industrial and research applications. Examples of the application of NAATs include, but are not limited to: determining whether a pathogen is present in a sample, quantifying the amount of virus in a sample, comparing the relative levels of two or more genes in a sample or determining the level of expression of a specific marker in a sample.

The prior art has described a variety of thermocycling and isothermal techniques for amplification of nucleic acids. Thermocycling techniques, such as the polymerase chain reaction (PCR), use temperature cycling to drive repeated cycles of DNA synthesis leading to large amounts of new DNA being synthesised in proportion to the original amount of template DNA. A number of isothermal techniques have also been developed that do not rely on thermocycling to drive the amplification reaction. Isothermal techniques, which utilise DNA polymerases with strand-displacement activity, have been developed for amplification reactions that do not involve an RNA-synthesis step. Similarly, for amplification reactions that do involve an RNA-synthesis step, isothermal techniques have been developed that may use reverse transcriptase, RNase H and/or a DNA-dependent RNA polymerase (see for example, Nucleic Acid Isothermal Amplification Technologies—A Review. Nucleosides, Nucleotides and Nucleic Acids, Volume 27, Issue 3 Mar. 2008, pages 224-243).

Sample-Preparation is a Common Requirement for NAATs.

Where it is desired to determine the presence and/or level of a nucleic acid in a particular sample using a NAAT, it is commonly required that prior to performing the NAAT, the sample is subjected to some degree of pre-processing (referred to herein as 'sample-preparation') in order to make the nucleic acids present in the sample available to the NAAT in a condition that will allow a NAAT-based assay to function effectively.

In practice, sample-preparation can be a laborious, multi-step process requiring skilled personnel and infrastructure, expensive consumables, a wide array of reagents and solvents (often dangerous or harmful) and various pieces of equipment such as centrifuges and vacuum manifolds. The complicated nature of the process offers multiple opportunities for operator error (including sample contamination) and as a result sample-preparation is challenging to perform outside of specialist laboratories without the aid of expensive robotic/semi-robotic sample-preparation devices.

Methods which can simplify and reduce the cost of sample-preparation are therefore highly desired and would allow the application of NAAT-based technologies away from specialised laboratories in more challenging environment and economic settings. For example, improved sample-preparation methods could allow NAATs to be used in villages in Africa for HIV detection if the cost of effective sample-preparation is low, and the sample-preparation method is simple enough to be reliably performed by a non-expert in such a setting.

Principles of Sample Preparation

There are three general principles that may be associated with sample-preparation:
  i) Making nucleic acid physically available to a NAAT (sample lysis)
  ii) Removal/reduction of NAAT inhibitors
  iii) Concentration of nucleic acids For a NAAT to work at all, the nucleic acids in a sample must be in direct physical contact with the NAAT reagents. Since nucleic acids are generally found within cells or virus capsids and since such cells/viruses may be further embedded within a complicated matrix, the sample-preparation process must be able to sufficiently disrupt both the cells/virus capsids and any associated sample matrix to make nucleic acid available to the NAAT.

Further, the matrix in which the nucleic acid of interest resides may contain substances capable of inhibiting a NAAT, hence it may be necessary to remove or reduce such inhibitors in order for the NAAT to function adequately.

Further still, in a number of instances, the abundance of nucleic acid of interest in a sample may be very low per unit volume. In such instances, methods which can concentrate nucleic acids from a large volume into a smaller volume are advantageous; often such concentration of nucleic acid may, in itself, facilitate the purification of the nucleic acid from inhibitors.

Sample Lysis

Sample lysis, to make nucleic acids available, can be accomplished by mechanical means (reviewed in J. Brent (1998). Breaking Up Isn't Hard To Do: A cacophony of sonicators, cell bombs and grinders" The Scientist 12(22): 23) and non-mechanical techniques. Simple mechanical approaches include the use of a blender and homogenization by forcing cells through restrictive openings. Sonication is based on the exposure of a sample to high-frequency sound waves, and bead approaches are based on exposing cells to violent mixing in the presence of various beads.

Chemical disruption of samples is an alternative to mechanical disruption. Detergents are important chemical lytic agents that act by disrupting lipid bilayers and solubilising/denaturing proteins. Sodium dodecyl sulphate (SDS), an ionic detergent, is commonly used in forensic DNA extraction protocols due in part to its ability to solubilise macromolecules and denature proteins within the cell (J. L. Haines et al (2005) Current Protocols in Human Genetics Vol. 2, (2005 John Wiley and Sons, Inc. Pub.). Proteinase K is often used in tandem with detergent-based (e.g. SDS, Tween-20, Triton X-100) lysis protocols to facilitate cell lysis. Another form of detergent lysis is based on FTA paper (U.S. Pat. No. 6,958,392). This is a cellulose filter impregnated with a weak base, an anionic detergent, a chelating agent, and preservatives.

Chaotropic agents such as guanidinium hydrochloride can also act as effective sample lysis agents, conveniently, these also allow for a means to purify nucleic acid as discussed further below.

A still further approach to lysis is the use of heat to break open cells/viruses. This physical approach has the benefit of requiring very simple hardware (just a heating block or water bath). Heat can be used in conjunction with other chemical lysis reagents to improve the lysis efficiency of difficult to lyse cells such as certain Gram positive bacteria and spores. The benefit of the chemical and heat lysis methods is that they are especially efficient at inactivating nucleases that can degrade the nucleic acid of interest. Further, they inactivate proteases which can harm the enzymes used in NAATs.

NAAT Inhibitors

The exploitation and utility of NAATs is significantly and adversely affected by a wide range of substances that act to negatively impact the performance of a NAAT (see, for example, "Capacity of Nine Thermostable DNA Polymerases To Mediate DNA Amplification in the Presence of PCR-Inhibiting Samples, Appl. Environ. Microbiol. October 1998 vol. 64 no. 10 3748-3753" for a review of various inhibitor issues). Example inhibitors are haem from blood, humic acid found in plants and soil, polyphenols, certain divalent metals and collagen. Since almost all biological samples contain NAAT inhibitors, it is clearly necessary to process samples prior to performing a NAAT so as to remove or reduce the level inhibitors. This is especially so with certain complicated and heterogeneous matrices such as faeces which have a very high load of inhibitory substances.

Inhibitor Removal

The removal or reduction of NAAT inhibitors can be achieved by i) actively separating nucleic acid from inhibitors using some property of the nucleic acid and/or inhibitor respectively ii) diluting the sample to bring the concentration of inhibitors below that which adversely affects the NAAT employed or iii) adding a liquid-phase additive which neutralises the inhibitory effect of the inhibitor.

For example, Chelex-100 (Bio-Rad, Hercules, Calif.) is a modified resin that efficiently binds multivalent metal cations which can inhibit NAATs (Walsh P. S. et al., Chelex 100 as a medium for simple extraction of DNA for PCR-based typing from forensic material. Biotechniques 10(4):506-13).

Polyvinylpolypyrrolidone (PVPP) is an insoluble highly cross-linked modification of polyvinylpyrrolidone (PVP) that has been used for the removal of polyphenols, such as humic acid, during DNA extraction (Holben W. E., Jansson J. K., Chelm B. K., Tiedje J. M. (1988) DNA Probe Method for the Detection of Specific Microorganisms in the Soil Bacterial Community. *Appl. Environ. Microbiol.* 54(3): 703-711).

We have identified a range of ion exchange resins useful for faecal inhibitor removal. These include but are not limited to: Optipore SD-2 (Dowex), an aminated styrene-divinylbenzene resin used for decolourisation and Diaion WA30 (Mitsubishi Chemical), a weakly basic, highly porous anion exchange resin. We have found that these resins can substitute for PVPP in the removal of NAAT inhibitors from faecal lysates. Activated charcoal is a further material that can be used to remove NAAT inhibitors. Preferably the activated charcoal will be in a form where it cannot pass through frits or filters used to retain it, for example, the activated charcoal may be in the form of large particles or beads. In general, combinations of resins and frits or filters can be selected such that the frits or filters do not become blocked by the resins whilst retaining the resin or other solid phase material used.

An alternative approach is to use size exclusion chromatography to separate high molecular weight nucleic acid from low molecular weight NAAT inhibitors. For example the illustra MicroSpin™ G-25 spin columns from GE Healthcare can be used to this effect.

Whilst perhaps the simplest approach to NAAT inhibitors is simply to dilute a sample to the point that inhibitor concentrations are too low to adversely affect a particular NAAT, this has the disadvantage of also diluting any nucleic acid in the sample. Hence, where the nucleic acid may be limiting (such as in pathogen detection), the dilution approach can result in false negative results being obtained in NAAT-based assays. To some extent, the dilution approach can be improved by adding liquid phase reagents which neutralise certain inhibitors. For example, EDTA may be added to a sample to bind to and make unavailable for the NAAT, certain inhibitory divalent metals (e.g. $Ca^{2+}$) and, in so doing, reduce the amount of dilution of the sample necessary to allow the NAAT to be employed. In fact, for some clinical applications where the numbers of organisms to be detected by a NAAT is at a very high level, samples can be diluted in a buffers containing EDTA by a factor where the inhibitor concentration is too low to inhibit amplification but where the amount of target present in the reaction is sufficient for reproducible detection. However, in very inhibitory sample types (for example, human faeces), a dilution factor in the order of 500 fold is often required even with EDTA to reduce inhibitor levels to a point where a NAAT can be employed; so clearly this approach is not ideal as such a large dilution would certainly impact the sensitivity of a NAAT-based test. Further, excessive amounts of EDTA can themselves be inhibitory to NAATs if carried over into the NAAT-based assay since EDTA can chelate the $Mg^{2+}$ required as a co-factor by DNA/RNA polymerases.

Nucleic Acid Purification

Where sample-preparation involves specifically purifying nucleic acids, this both removes NAAT inhibitors but can also concentrate the nucleic acid from the sample.

In this approach, a unique property of nucleic acids is used to separate them from other constituents of the sample (including inhibitors) and allow the nucleic acids to be concentrated into a buffer of choice. This has the significant advantage of increasing the sensitivity of NAAT-based tests. For example, if the nucleic acid from HIV contained in 1 ml of blood can be concentrated into just 20 µl then this could offer up to a 50 fold increase in the concentration of HIV nucleic acid, post sample-preparation: this could make the difference between a particular NAAT detecting HIV or not.

One of the earliest nucleic acid purification methods was the use of phenol/chloroform extraction (D. M. Wallace (1987) Large and small scale phenol extractions. Methods Enzymol. 152:33-41; Maniatis, T. et al., "Purification of Nucleic Acids" in Molecular Cloning: A Laboratory Manual, 3rd Ed. Cold Spring Harbor Laboratory, Cold Spring Harbor, N.Y.). In this method, most protein moves to the organic phase or the organic-aqueous interface, and solubilized DNA remains in the aqueous phase. The DNA-containing phase can be subjected to ethanol precipitation, and DNA isolated following a series of centrifugation and wash steps. The advantage of the organic extraction approach is that it yields high quality DNA preparations (with relatively low amounts of protein and relatively low degradation) and remains one of the most reliable methods available today.

The major disadvantages are that the procedure is time- and labour-intensive, uses dangerous solvents and reagents, requires cumbersome equipment, and is relatively difficult to adapt to high-throughput settings and certainly not suitable for near-patient testing, or for use by an unskilled operator.

An alternative approach to nucleic acid purification is the use of silica in conjunction with a chaotropic agent (Boom, R. et al., (1990) "Rapid and Simple method for purification of nucleic acids," J Clin Microbiol. 28(3):495-503). The chaotropic agent acts to both lyse cells/viruses but also acts to cause nucleic acids to bind silica particles. The nucleic acid can be subsequently eluted from the silica using a low-ionic strength buffer (or water). The Boom method forms the basis of a number of lysis/purification approaches widely (e.g. DNAIQ Systems, Promega, Madison, Wis.). An alternative to silica beads is the use of silica membranes (QIAamp, Qiagen Hilden, Del.). In addition, the silica beads themselves may be modified to further enhance DNA binding.

An alternative charge-based approach is the use of ion exchange resins. A solution containing DNA and other macromolecules is exposed to the ion exchange resin. The negatively charged DNA (due to its phosphate backbone) binds relatively strongly to the resin at a given salt concentration or pH. Protein, carbohydrate, and other impurities bind relatively weakly (if at all) and are washed from the beads (e.g. in a column format or by centrifugation). Purified DNA can then be eluted in a high ionic strength buffer. A commercially available anion exchange resin used today is based on DEAE-modified silica beads (Genomic-tip, Qiagen).

A related approach to that of ion exchange resins is to use modify solid matrices that have a net positive charge at a given pH and are capable of binding DNA (Baker, M. J., U.S. Pat. No. 6,914,137). The modification contains an ionizable group, such that the DNA binding is reversed at a higher pH (when the ionisable group is neutral or negatively charged). A widely used approach of this type is based on the ChargeSwitch bead (Life Technologies, Inc. Carlsbad, Calif.).

Oligonucleotide Capture

Target nucleic acids can also be isolated through the use of capture oligonucleotides. In this method sample nucleic acid are incubated with a capture oligonucleotide that hybridises with complementary target sequence in the target. The hybridised target-capture oligonucleotide complexes are then pulled out of solution and washed to remove impurities. This can either be achieved by ligand-receptor interaction, such as biotin-streptavidin where the capture oligo oligonucleotide is biotinylated, and can be used in a number for formats including magnetic beads, coated tubes, etc. The captured target can then be directly added to the amplification reaction. An example of the use of oligonucleotide capture is the APTIMA HIV assay (Gen-Probe).

Immunomagnetic Separation (IMS)

Specific cell types can also be isolated using antibodies bound to paramagnetic particles directed towards their specific surface epitopes. Target cells/viruses are removed from the sample by the application of a magnetic field and added to a detection assay for the organism. An example of the use of IMS is the detection of *Salmonella* by the Pathatrix system (Matrix MicroScience Ltd). (Odumeru J. A., & Carlos G. León-Velarde C. G. (2012) *Salmonella* Detection Methods for Food and Food Ingredients. in *Salmonella—A Dangerous Foodborne Pathogen*, Ed. Barakat S. M. Mahmoud. InTech, Rijeka, Croatia.)

Magnetic Beads

One skilled in the art will recognise that magnetic beads or particles can be used for ChargeSwitch, oligonucleotide capture and immunomagnetic separation. The Boom method can also be implemented using magnetic particles or beads containing both silica and magnetic iron oxide (Berensmeier S. (2006) Magnetic particles for the separation and purification of nucleic acids. *Appl. Microbiol. Biotechnol.* 73(3): 495-504). An example of magnetic particle Boom extraction is the NucliSENS systems (bioMérieux).

Sample Preparation Protocol Challenges

The three discussed aspects of sample-preparation, extraction, inhibitor removal, nucleic acid purification/concentration, inevitably result in multi-step procedures. Each step in the procedure adds time and effort and introduces complexity, cost and operator error. Even for specialist laboratories with highly trained operators, the complicated nature of present sample-preparation methods means that manual approaches are simply too cumbersome to employ and some form of automation is therefore required.

Away from specialist laboratories, there may not be the infrastructure or skilled operators to perform sample-preparation. To address this need, technologies have been introduced that allow the discrete automation of sample preparation so that NAAT assays can be performed by non-expert users. However, such approaches require complicated and costly consumables which may exclude their use from certain environments where there are economic constraints on purchasing expensive sample-preparation methods.

A variety of laboratory robotic instruments have been developed for the partially automated purification of nucleic acids. For example, the Maxwell 16 instrument (Promega) iPrep instrument (Life Technologies), NucliSENS easyMAG (bioMérieux) and Qiagen EZ1, BioRobot M48 and Qiacube systems (Qiagen) are designed to purify nucleic acids from a range of clinical and forensic sample types. Some of these systems require some manual preprocessing before loading of samples onto the instrument. The Innuprep (analytikJena, Itzehoe, Del.), LabTurbo (Taigen, Taipei, TW), Xiril 150 (Xiril AG, Hombrechtikon, CH), and Quickgene (FujiFilm Corp., Tokyo, JP) extraction systems all require more manual handling than the aforementioned fully robotic systems.

More completely automated systems have been used for both clinical and forensic detection. Most notable is the Cepheid (Sunnyvale, Calif.) GeneXpert system that for *C. difficile* performs DNA extraction and real-time PCR originating from a faecal swab specimen. However, the cost of both the equipment and for a single test can be prohibitively high for many organisations.

Using Pressure to Prepare Samples

A number of methods exist which use pressure or pressure differences to move liquids between compartments as part of the sample preparation process. For example, the following documents describe methods which use pressure as part of the sample preparation process:

GB2337261 discusses the purification of nucleic acids from whole cells using a porous membrane filter under pressure.

JP 2005095003 teaches a cartridge for separating and purifying nucleic acids by passing the sample solution through by a pressure difference.

JP 2005118020 teaches a cartridge containing a nucleic acid adsorbing porous material having at least two openings and apparatus to generate a pressure difference between at least two openings.

US 20070269829 discusses a nucleic acid isolation instrument which includes a pressurization device and comprises first and second container portions that are connected via a solid phase.

US 2009/0023904 teaches a cartridge which includes a container that has at least two openings and contains a nucleic acid adsorbent solid phase. The pressure difference is applied across the solid phase.

U.S. Pat. No. 5,804,684 teaches contacting a biological sample with a nucleic acid binding matrix (agarose particles in liquid suspension) which causes nucleic acid to precipitate; and eluting from matrix.

US 2008/0275228 teaches injecting liquid into cartridge for isolation and purification of nucleic acids and passing the liquid through a nucleic acid adsorbent solid phase by a pressure difference.

US 2009/0023201 discusses a nucleic acid-detecting cassette and water soluble agglomeration resistant organic compounds.

An advantage of such methods is that they can avoid the use of equipment such as centrifuges in the sample preparation process. For example, pressure can be used to move liquids around a device so as to facilitate sample preparation. However, a disadvantage of such methods is that complicated consumables or pumps are still required to process the sample.

SUMMARY

Sample-preparation represents an essential component of NAAT-based assays. Depending on the sample type, the level of inhibitors and any requirement to concentrate the nucleic acids in the sample, sample-preparation may represent the most onerous and costly part of performing a NAAT-based assay.

In order for the benefits of NAAT-based assays to be enjoyed by those without access to specialist equipment or personnel or to those who cannot afford expensive automated systems, there is a need for simpler methods which are not costly, can be performed by non-expert users and which do not require sophisticated hardware. Whilst methods exist which remove the need for equipment such as robots, centrifuges or vacuum manifolds to prepare samples by the use of pressure to move liquids within a device, such methods are still encumbered with either complicated consumables or hardware to generate pressure differences. Further, methods which take advantage of low-cost, easily accessible physical methods to effect sample preparation (in particular heat) have yet to be fully exploited. As the generation of moderate heat is extremely easy, a sample-preparation method which can be heat-driven yet combine more sophisticated chemistries associated with sample-preparation could make the preparation of samples for NAAT-based assays more readily achieved at lower cost and with far less complicated hardware. Such a sample-preparation method could enable NAAT-based assays to be performed in more challenging environments for example in small clinics in low-resource settings.

DETAILED DESCRIPTION OF THE PREFERRED EMBODIMENTS

The inventors have discovered that it is possible to elute a liquid from a sealed container by heating the container to a temperature which creates sufficient pressure to elute the liquid from the container. The invention thus provides a method for passing a liquid sample through a porous solid matrix, comprising the steps of sealing the liquid sample within a container which comprises a porous solid matrix as at least a part of the container and raising the temperature to increase the pressure inside the container, thereby to cause the liquid to pass through the porous solid matrix. By passing the liquid through the porous solid matrix, at least part of the liquid can be removed from the container. The methods of the invention also allow the liquid to be transferred from the container to a second container or to a vessel.

The process of using heat to pass a liquid sample through the porous solid matrix is referred to herein as "Heat-Elution".

It was advantageously found that sufficient pressure could be generated to pass a liquid through a porous solid matrix from a container at temperatures of less than 110° C., even with a variety of different container sizes. This could be achieved using standard plastic consumables despite the presence of a porous solid matrix in the container which blocks the flow of liquid out of the container at room temperature. That such gentle temperature and pressure conditions can be used, means that nucleic acids are not damaged in the process nor is there any significant danger of the container acquiring sufficient pressure to fail or even explode, nor are extremely hot heating devices (>110° C.) required. Accordingly, the invention provides improved methods of sample preparation, in particular before performing a NAAT-based assay.

A further advantage of the methods of the invention is that the number of steps (in particular liquid transfer steps) required to perform sample-preparation is much reduced compared to other methods. For example, in embodiments using porous solid matrices which bind NAAT inhibitors more strongly than nucleic acids, the operator must simply 1) transfer the sample into the first container,
2) perform Heat-Elution, and
3) use the eluted nucleic acids in a NAAT-assay.

There are no additional liquid transfers required. Further, this can be achieved with only the use of the container itself and a heating block. No additional centrifuges, pumps or vacuum systems are required. This greatly reduces the hardware infrastructure required to perform sample-preparation as well as reducing the complexity of the sample-preparation process such that it can be readily performed by a non-expert operator.

The temperature can be increased to temperatures of up to 110° C. The inventors have found that heating the sealed container up to 110° C. creates sufficient pressure to pass the liquid sample through the porous solid matrix, irrespective of the size of the container. The temperature can also be increased to temperatures which are below 110° C., for example to a temperature below 100° C., below 90° C., below 80° C. or below 70° C. The minimum temperature for passing the liquid sample through the porous solid matrix can differ between different containers and can be, for example, at least 40° C., at least 50° C. or at least 60° C. In general, the temperature will be increased to temperatures above room temperature. The precise temperature can be easily determined experimentally by subjecting a container to increasing temperatures and establishing the temperature at which the liquid sample is passed through the porous solid matrix. Where the heat employed will also be used to lyse cells or viral capsids, then the temperature which is sufficient to lyse said cells or viral capsids can be easily determined experimentally. However, in general a temperature of at least 90° C. would be necessary.

In accordance with the invention, all of the liquid sample which was added to the container may be passed through the porous solid matrix. Methods in which at least 20%, at least 30%, at least 40%, at least 50%, at least 60%, at least 70%, at least 80%, or at least 90% of the original volume of the liquid sample is passed through the porous solid matrix are also within the scope of the invention. The liquid sample which is passed through the porous solid matrix may have a different composition compared with the composition of the liquid sample which is added to the container. For example, the eluted sample may have a lower content of NAAT inhibitors compared with the liquid sample which was added to the container.

Heat-elution can be practised by exposing the container to a heating device which has the temperature to which the container is to be heated. Alternatively, it is also possible to gradually increase the heat in the container until the desired temperature has been reached. Further still, the container could be subjected to radiation such as microwaves or infra-red.

As the liquid is passed through the porous solid matrix by the pressure created by heating the container, it is understood that Heat-Elution in accordance with the invention can be performed in the absence of further external forces, such as centrifugation or the application of a vacuum (for example via a vacuum pump).

In accordance with the invention, the container will be sealed. Ways of sealing a container are known in the art. For example, the container can be sealed using a lid, or a stopper. Alternatively, it is also possible to seal the container by fusing the edges of an opening in the container, for example by heating the opening and pressing the edges together. This may be particularly relevant where the container is made from plastic or other thermoplastic materials as it would easily be possible to heat the opening and fuse the edges of the opening by application of pressure. This can be achieved, for example, by using heated jaws. As the Heat-Elution methods of the invention require the liquid to be passed through the porous solid matrix it is understood that at least part or all of the porous solid matrix will not be sealed as otherwise the liquid could not pass through.

The methods of the invention may comprise a further step of adding the liquid sample to the container.

The Container

In the context of this specification, a "container" is a vessel which is suitable for Heat-Elution.

In general, the container comprises a porous solid matrix as at least a part of the container. The porous solid matrix can be arranged such that it is in communication with both the inside and the outside of the container. This allows the liquid sample to be transferred from the inside to the outside of the container when the liquid sample is passed through the porous solid matrix.

The porous solid matrix may be an integral part of the container and can form, for example, at least part of a wall of the container. It is also possible that the porous solid matrix does not form an integral part of the container. In these embodiments, the container will comprise an opening and the porous solid matrix will be positioned relative to the opening so that the porous solid matrix is in communication with both the inside and the outside of the container.

A container can comprise one or more openings which are suitable for adding the liquid sample to the container. In accordance with the methods of the invention, these one or more openings need to be sealed in order to seal the liquid sample within the container.

A "vessel" is any vessel which is suitable for containing a liquid but which is not suitable for Heat-Elution.

Porous Solid Matrix

The container will comprise at least one porous solid matrix which can retain the liquid within the container at room temperature (e.g. at 18-22° C.) but allows the liquid to pass through when the pressure in the container increases due to the increased temperature.

In some embodiments, the container comprises only one type of solid porous matrix. The methods of the invention can also be practised with containers which comprise two or more different porous solid matrices. For example, the container may comprise a first porous solid matrix and a second porous solid matrix. The first porous solid matrix preferably retains the liquid in the container before the container is heated. The first porous solid matrix can be a filter. The second porous solid matrix can be a matrix which binds NAAT inhibitors more strongly than nucleic acids, or which binds nucleic acids more strongly than NAAT inhibitors. The second porous solid matrix can be added to the container before the liquid is added and/or it can be pre-mixed with the liquid and added to the container together with the liquid sample. The second porous solid matrix may be in the form of beads, for example magnetic beads.

The porous solid matrix can be a filter. The porous solid matrix (in particular the second solid porous matrix where more than one type of matrix is used) can be a matrix which binds NAAT inhibitors more strongly than nucleic acids, or which binds nucleic acids more strongly than NAAT inhibitors. Such porous solid matrices are preferred because the methods of the invention can then either act to remove inhibitors of nucleic acid amplification from nucleic acids or, conversely, they may act to purify and/or concentrate nucleic acids from a sample.

In this respect, the porous solid matrices need to bind at least one inhibitor of nucleic acid amplification more strongly than nucleic acids or vice versa in order to be suitable for use in the methods of the invention. Whether a particular porous solid matrix binds inhibitors of nucleic acid amplification more (or less) strongly than nucleic acids can be determined by contacting a sample comprising inhibitors of nucleic acid amplification and nucleic acids with the matrix and separating the liquid from the matrix. If the relative decrease of the inhibitors compared to the relative decrease of the nucleic acids in the separated liquid is higher, the matrix binds the inhibitors more strongly.

The porous solid matrix may be in the form of a resin or in the form of beads, for example magnetic beads.

Removal of NAAT Inhibitors

Where the porous solid matrix binds NAAT inhibitors more strongly than nucleic acids, the desired nucleic acids will be preferentially eluted from the matrix. The inventors have surprisingly discovered that they can remove NAAT inhibitors more efficiently if i. the porous solid matrix is heated with the liquid sample rather than being mixed at room temperature alone, and ii. the liquid sample comprises unbound nucleic acids which are separated from the porous solid matrix whilst the matrix and the liquid are still heated.

The improved ability to remove NAAT inhibitors requires only heating as described above and does not rely on the elution due to the pressure generated by the heat.

Thus, the invention provides a method for purifying nucleic acids from a liquid sample which comprises nucleic acids and inhibitors of nucleic acid amplification, wherein the method comprises the steps of (a) contacting the sample with a porous solid matrix which binds inhibitors of nucleic acid amplification more strongly than nucleic acids, wherein heat is applied to the porous solid matrix and the liquid sample; and (b) separating the liquid sample comprising unbound nucleic acids from the porous solid matrix.

In the methods according to this aspect of the invention, it is understood that the method will be performed under conditions in which at least some of the NAAT inhibitors bind to the porous solid matrix while at least some of the nucleic acids will not bind to the porous solid matrix. Suitable conditions will be known to the skilled person.

Heat may be applied in step (b).

The methods of this aspect of the invention may be practised using Heat-Elution in accordance with the invention using a container which comprises a porous solid matrix as at least a part of the container. Thus, the method may comprise the steps of sealing the liquid sample within the container and raising the temperature to increase the pressure inside the container, thereby to cause the liquid to pass through the porous solid matrix.

It has been shown that the gentle pressure generated by Heat-Elution, compared to centrifugation, means that fewer inhibitors are moved off the porous solid matrix phase material. In fact, if centrifugation is used to pass a liquid through the porous solid matrix, the nucleic acid sample found in the second vessel will contain more inhibitors of nucleic acid amplification than when using Heat-Elution. Furthermore, the improved inhibitor removal means that the overall dilution factor of the sample-preparation can be reduced. As such the methods of the invention do not require the dilution of the original sample as much as methods which do not employ principles i) and ii) above.

The force of the pressure elution is insufficiently high to cause significant shearing of genomic DNA that is seen with centrifugal column methods. Consequently, it is unlikely that the target region in the relevant sample DNA molecules will be interrupted by shearing and therefore compromise detection.

Preferably, the liquid sample is separated from the porous solid matrix whilst the liquid sample still has a temperature of more than 60° C., more preferably the temperature is more than 70° C., even more preferably the temperature is more than 80° C., and most preferably the temperature is more than 90° C. The sample and the matrix in step (a) may be heated for 1 to 10 minutes.

Several types of porous solid matrices, including ion-exchange resins, have been found to function as the porous solid matrix according to this aspect of the invention. These resins are capable of sequestering one or more NAAT-inhibitor(s). These porous solid matrices include but are not limited to styrene-divinylbenzene co-polymers containing iminodiacetic acid (such as Chelex 100-Bio-Rad), PVPP (Polyvinylpyrrolidone), Polystyrene-Base Dimethylamine based resins (Diaion WA30– Mitsubishi Chemical), macroporous styrene divinylbenzene copolymers with tertiary amine functionalised groups (Optipore SD2, Dowex) and highly porous weak base anion exchange resins consisting of a styrene-divinylbenzene matrix with tertiary amine functionalised groups (SDVB family of resins). Activated Charcoal may also be used. Such matrices can be used individually or in combination with each other. It is understood that a person skilled in the art would be able to screen matrices or mixtures of matrices that will give the best removal of NAAT inhibitors from a particular sample matrix using the methods of the present invention.

Certain matrices such as Chelex 100, are known to chelate divalent metal ions, others such as PVPP are known to bind to inhibitor polyphenol compounds. It is understood that a person skilled in the art would screen for matrices which have a higher affinity for NAAT inhibitors than for nucleic acids such that, following Heat-Elution, nucleic acids are separated from NAAT inhibitors. For example, for the detection of *Clostridium difficile* DNA from human faeces, the present inventors have found the following combination of resins to be particularly effective for removing NAAT inhibitors without binding to *Clostridium difficile* DNA such that this DNA is conveniently found in the second vessel following Heat-Elution is 10% v/v Chelex 100, 25% v/v Optipore SD-2 and 25% v/v Diaion WA30 in 1.9 ml of reaction buffer.

NAAT inhibitors are known in the art and include, for example, haem from blood, humic acid found in plants and soil, polyphenols, and certain divalent metals, such as calcium or collagen.

The nucleic acids purified according to this aspect of the invention can be added directly to NAAT reagents to perform a NAAT assay. The eluted nucleic acids may also be further processed before performing a NAAT assay. For example, the nucleic acids may be subsequently concentrated and/or transferred into a different buffer. Suitable concentrations methods are well known in the art.

Nucleic Acid Capture Strategies

Where the porous solid matrix binds nucleic acids more strongly than NAAT inhibitors, the nucleic acids are preferentially retained on the matrix in the container following Heat-Elution and the NAAT inhibitors are preferentially passed through the porous solid matrix with the liquid sample. Thus the invention provides a method of purifying nucleic acids from a liquid sample using a container which comprises a porous solid matrix as at least a part of the container, wherein the method comprising the steps of sealing the liquid sample within the container and raising the temperature to increase the pressure inside the container, thereby to cause the liquid to pass through the porous solid matrix, wherein the porous solid matrix binds nucleic acids more strongly than inhibitors of nucleic acid amplification It is understood that, using such porous solid matrices, at least some of the nucleic acids will be retained by the porous solid matrix while the liquid phase, including at least some of the NAAT inhibitors, will be largely or completely eluted. Subsequently, it can be necessary to further process the nucleic acids which were retained by the porous solid matrix to make them available for a NAAT. This can be done, for example, by opening the container and adding a buffer which will elute bound nucleic acids from the porous solid matrix and performing Heat-Elution to elute at least some or all of the bound nucleic acids from the porous solid matrix into a vessel. The vessel contains eluted nucleic acids which can be used in a NAAT assay.

Examples of solid phase materials that can be used for this aspect of the invention include silica (via the described Boom-based extraction process), Charge-Switch beads, oligo-capture beads and ion-exchange resins/beads.

Where porous solid matrices are used to capture and/or concentrate nucleic acids, the invention reduces the complexity of the sample-preparation process. The fact that, following Heat-Elution, all the liquid sample can be transferred into a second container or a vessel means that nucleic acids can be eluted from or removed from the container with minimal contamination from the original liquid phase (containing inhibitors) which makes further processing of the sample easier. In some cases, an elution buffer can be added directly to the porous solid matrix following the initial Heat-Elution step in order to elute the bound nucleic acids from the matrix so that the nucleic acids can be immediately added to NAAT reagents. It is understood that for some NAATs (in particular where bioluminescent reporter systems are used such as described in WO2004/062338) the porous solid matrix with the bound nucleic acids can be transferred directly into NAAT reagents as such methods are tolerant to such solid phase material.

Alternatively, it is possible to perform a second Heat-Elution step to elute at least some of the nucleic acids or all of the nucleic acids from the porous solid matrix. This conveniently allows for further processing of the sample using the same principle.

The Liquid Sample

The sample which is passed through the porous solid matrix in accordance with the invention is a liquid sample. The term "liquid sample" does not exclude that the sample may comprises some solid components but it is understood that the majority of the volume of the sample (for example at least 70%, at least 85%, at least 95% or at least 99%) is liquid.

The liquid sample may be derived from a starting sample which is itself a liquid sample, such as for example plasma or urine. The starting sample on which NAAT may be performed and from which the liquid sample may be derived can be also a solid or semi-solid sample. For example, the sample may be a faecal sample, food sample or tissue sample. For such samples, the solid or semi-solid sample may be mixed with a suitable buffer prior to being introduced to the container to provide the liquid sample. Alternatively the solid or semi-solid sample may be added to a container which has been pre-loaded with a suitable buffer thus resulting in a liquid sample. The solid or semi-solid sample may also be mixed with a suitable buffer before introduction to the container and then subsequently mixed with a second suitable buffer (or the same buffer) pre-loaded in the container.

The starting material may also be a liquid sample which can be added directly to the container. The liquid sample may be mixed with a suitable buffer prior to being introduced to a container in accordance with the methods of the invention. Alternatively the liquid sample may be added to a container which has been pre-loaded with a suitable buffer. The liquid sample may also be mixed with a suitable buffer before introduction to the container and then subsequently mixed with a second suitable buffer (or the same buffer) which was pre-loaded in the container.

In the methods of the invention, the porous solid matrix may be pre-loaded in the container or introduced into the container together with or following the sample itself. The porous solid matrix may be in the form of a resin or beads, such as magnetic beads.

The liquid sample may comprise a buffer which maximises the effectiveness of the sample preparation and/or the nucleic acid purification. Suitable buffers may comprise components which can, for example, protect nucleic acids from degradation, facilitate the sample preparation and/or make the sample-preparation compatible with the NAAT reagents which are subsequently used. For example, the buffer may comprise EDTA or Bovine Serum Albumin which are inhibitor removal agents. It may also comprise one or more protease(s) which can facilitate the lysis of the sample and which can inactivate enzymes, such as nucleases. It may also contain detergents or salts (such as KCl) which facilitate both sample-preparation and subsequent nucleic acid amplification. The buffer may also be configured to maintain the pH of the liquid sample at a pH which is useful for sample preparation, for example at a pH of 4.5-9.5, or a pH of about 8.

Sample Lysis

The heat employed in the methods of the present invention may also function to lyse samples in the container and so make available nucleic acids for a subsequent NAAT-based assay. Thus, the methods of the invention may include a step of lysing the sample. A lysis step is particularly preferred where the liquid sample comprises bacteria (such as spore-forming bacteria) and/or viruses because the lysis of bacteria or viruses can also render said bacteria or viruses non-infectious and hence represents a convenient safety feature of the present invention. The effectiveness of heat to lyse samples can be significantly increased by the addition of other reagents and/or by certain solid phase materials. For example, EDTA and Chelex have been shown to facilitate cell membrane lysis by sequestering divalent ions which stabilise lipid bilayers (Brown, T. A. (1995) Gene cloning: an introduction. 3rd Ed. Chapman & Hall).

The methods of the invention can also be used with liquid samples which have been lysed before the liquid sample is added to the container. This is particularly advantageous for samples which are difficult to lyse by heat alone. For example, for certain spore-forming bacteria, it may be advantageous to first use a mechanical method to break open the spores. Means for lysing samples are known in the art and include, for example, sonication, mechanical homogenization (for example, by using blenders, forcing cells through restrictive openings, or violent mixing in the presence of various beads), and chemical disruption, for example, through the use of detergents (such as sodium dodecyl sulphate (SDS), optionally in combination with proteinases such as Proteinase K) or chaotropic agents (such as guanidinium hydrochloride).

Where the eluate of the Heat-Elution process is to be directly added to NAAT reagents, it can be important that the eluted liquid has cooled sufficiently so as not to adversely affect the NAAT reagents. This is especially important when using isothermal NAATs wherein some of the enzymes used cannot tolerate higher temperatures. For example, for some NAATs, such as Nucleic acid sequence based amplification (NASBA) and rolling circle amplification (RCA), the temperature of the sample must be below 50° C., or even below 40° C. in order for the NAAT to work. For NAATs using strand-displacing polymerases such as Bst Polymerase or related polymerases, for example, Loop mediated isothermal amplification (LAMP) or strand displacement amplification (SDA), the temperature of the sample must be below 90° C., 80° C., 70° C. or even 60° C. for the NAAT to work. Thus, in some aspects of the invention the liquid sample is cooled to temperatures below 90° C., below 80° C., below 70° C., below 60° C., below 50° C. or even below 40° C. before the eluted sample is mixed with NAAT reagents.

Following Heat-Elution, the liquid sample may be eluted into a second container or a vessel, wherein the container or the vessel are at substantially the same temperature as the container which was used for Heat-Elution, such that the eluted liquid remains heated after Heat-Elution. The second container or the vessel may also be at a lower temperature than the first container. For example, the temperature could differ by up to 100° C., e.g. where a vessel is kept at 4° C. to help preserve the eluted nucleic acids from degradation.

The container or the vessel may also be actively cooled following Heat-Elution.

Control of Elution

Where the methods involve the lysis of the sample in the container, it is important that the sample is heated to a sufficient temperature for a sufficient time for the physical process of sample lysis to occur. Similarly, there must be sufficient time for the lysed sample to interact with the provided solid phase material before elution occurs.

As such, the inventors have realised that it can be necessary to control the elution speed of the liquid sample from the container such that the liquid sample spends a sufficient amount of time in the container at the required temperature. This can be achieved by restricting the flow of liquid from the container, which can be done by a variety of means. Thus, in some aspects of the invention the container will comprise a flow restrictor which is configured to reduce the flow of liquid from the container through the porous solid matrix compared to a container which does not have the flow restrictor. In particular, such flow restrictors can reduce the flow of liquid from the container through the porous solid matrix compared to a container which does not have the flow restrictor when the container is heated to a temperature above room temperature (for example above 40° C. or above 50° C.). The flow restrictors may act by either allowing constant, yet limited, flow of liquid through the porous solid matrix when heat is applied to the container. Suitable examples of such flow restrictors are filters and frits. The flow restrictor may also reversibly seal the porous solid matrix. In this aspect of the invention, the seal will be removed before the liquid sample can be eluted from the container. This can be achieved, for example, by valves which may be actuated by a mechanical, magnetic or electrical control system. The flow restrictor may also be a layer of material which melts at a temperature above room temperature but below 110° C., for example at a temperature between 45° C. and 110° C., between 55° C. and 110° C. or between 65° C. and 110° C. Suitable materials are thermoplastic polymers or waxes (i.e. compounds which melt above 45° C. to give a low viscosity liquid), for example paraffin wax.

Nucleic Acid Amplification Techniques

The methods of the invention can be used to prepare samples for any NAAT. Thus, while the invention has been particularly exemplified using the method known as loop-mediated isothermal amplification (LAMP; Notomi et al. Nucleic Acid Research, 2000, 28; E63) in conjunction with a bioluminescent reporter system known as BART (Gandelman et al. Public Library of Science, November 2010, Volume 5, Issue 11, e14155) it is to be understood that the methods are not limited to this NAAT. For example, the inventors have shown that nucleic acid samples prepared in accordance with the invention can also be used in polymerase chain reaction (PCR), which is to known to be more sensitive to inhibitors than LAMP. The methods of the invention can also be used to prepare samples for other NAATs, such as Template Re-priming Amplification (TRA), Self Extending Amplification (SEA), Nucleic acid sequence based amplification (NASBA), strand displacement amplification (SDA) and SMart Amplification Process (SMAP).

Further Heat-Elution Steps

Heat-Elution in accordance with the invention may be repeated more than once, for example two times, three times, four times, five times etc. Where Heath-Elution is performed more than once, this can be done by applying liquid to the same container which was used in the first Heat-Elution step. This can be necessary, for example, where the total volume of the liquid sample exceeds the volume of the container in order to purify all of the nucleic acids in the liquid sample. It can also be necessary where it is desired to wash the porous solid matrix after the nucleic acids have bound to it, or it may be necessary to apply an elution buffer in order to elute the bound nucleic acids from the matrix. In these methods additional containers or vessels may be used where required to collect the eluted liquid.

Where Heat-Elution is performed more than once, it may also be practised using more than one container. For example, the liquid from a first container may be eluted into a second container. The second container can then be sealed and the temperature raised to increase the pressure inside the container, thereby to cause the liquid to pass through the porous solid matrix. The eluted liquid from the second container can then either be discarded, collected in a vessel or transferred to a third container. Where two, three or more containers are used they can be heated either simultaneously, in tandem or in sequence to move the liquid sample from container to container in order to automate a number of sample-preparation processes within a single consumable. Where the containers are heated simultaneously it is possible to use containers with different wall thicknesses so that the sample and the matrices in the containers reach the desired temperature at different time points.

In some aspects, the liquid sample eluted by Heat-Elution from the container (whether this is the first, second, third or more Heat-Elution of a particular sample-preparation process) may be directly combined with NAAT reagents within a supplied container such that no additional liquid handling step (e.g. a pipetting step) is required to transfer the processed sample to NAAT reagents.

In this way, a single apparatus can be envisaged containing two for more containers whereby an operator has only to introduce a sample into one container to perform the entire sample-preparation process including mixing the processed sample with NAAT reagents. Such an apparatus would have the significant benefit of not requiring complicated pumps and centrifuges to move liquid from one container to another: a simple heating system could be used.

Apparatuses

As discussed above, the invention is particularly suitable for purifying nucleic acids in an automated setting using the methods of the invention. Thus, the invention provides apparatuses which are suitable for purifying nucleic acids in accordance with the methods of the invention. For example, the invention provides an apparatus for purifying nucleic acids, comprising (a) a container comprising a porous solid matrix as at least a part of the container and means for sealing the container, and (b) a heating element configured to heat the container to a temperature of up to 110° C. The apparatus may further comprise a second container to receive liquid passed through the porous solid matrix. In addition, or alternatively, it may also comprise a vessel comprising reagents for nucleic acid amplification.

The apparatuses of the invention allow the automated purification of nucleic acids from samples which can greatly facilitate sample preparation. Particularly in embodiments where the apparatus also contains a vessel comprising reagents for nucleic acid amplification, the apparatuses of the invention have the advantage that the operator only needs to add the sample to the apparatus because all subsequent steps can be performed automatically. Thus, a sample can be processed and amplified with no manual interventions between adding the sample to the container and recording the output of the amplification itself.

The container in the apparatus may comprise a porous solid matrix which binds nucleic acids more strongly than inhibitors of nucleic acid amplification, or which binds inhibitors of nucleic acid amplification more strongly than nucleic acids as discussed in detail above.

The apparatus may comprise two or more (for example two, three, four, five, six or more) containers. The porous solid matrices may be the same in all of the containers in the apparatus. They may also be different which can be advantageous in embodiments where the matrix captures inhibitors of NAAT because it would then be possible to have matrices which bind different inhibitors with different strengths, which can improve the removal of the inhibitors. Where more than one container is present in the apparatuses of the invention, it is preferred that each of the containers can be heated to temperatures of up to 110° C. by a heating element because then the liquid in these further containers can be transferred by heat alone. The apparatus may comprise one heating element or more than one heating element. The two or more containers in the apparatus may be heated at different rates and/or to different temperatures.

Where the apparatus comprises more than one container, or one or more containers and a vessel, the containers may be positioned within the apparatus so that the eluted liquid from one container drips directly into an opening of a further container or a vessel. It is also possible to transfer the liquid by a pathway, such as a tube. If the further container is to be used for Heat-Elution in accordance with the invention, the tube may contain, for example, a valve which allows for the container to be sealed before it is heated.

In accordance with the invention, the liquid from the container(s) will be passed through the porous solid matrices of the one or more containers by heat. Accordingly, it is preferred that the apparatuses of the invention will not comprise a centrifuge or a pump which is required for passing the liquid through the porous solid matrix of the container.

It is preferred that the apparatuses of the invention comprise a vessel which comprises at least some of the reagents, or preferably all of the reagents, which are required for NAAT. The vessel can be positioned within the apparatus in such a way so that the liquid eluted from a container is added directly to the vessel comprising the NAATs. The apparatuses of the invention are suitable for use with all NAATs, including but not limited to PCR and LAMP. The reagents which are required for the NAATs are known in the art and include, for example, one or more primers, a buffer, a polymerase and nucleotides (such as dNTPs).

General

The term "about" in relation to a numerical value x is optional and means, for example, x±10%.

The term "comprising" encompasses "including" as well as "consisting" e.g. a composition "comprising" X may consist exclusively of X or may include something additional e.g. X+Y.

The term "a" or "an" means "one or more".

Unless specifically stated, a process comprising a step of mixing two or more components does not require any specific order of mixing. Thus components can be mixed in any order. Where there are three components then two components can be combined with each other, and then the combination may be combined with the third component, etc.

BART refers to a method for determining the amount of template polynucleic acid present in a sample wherein the presence of inorganic phosphate which is derived from the amplification reaction is detected and is indicative of the amount of template polynucleic acid in the sample.

Various aspects and embodiments of the present invention will now be described in more detail by way of example. It will be appreciated that modification of detail may be made without departing from the scope of the invention.

DESCRIPTION OF THE FIGURES

FIG. 1

FIG. 1a shows the principle of adding a liquid sample to a container which contains another, sealed opening; sealing the opening to the container where the liquid was introduced; opening an exit to the container on the other side of some sort of filter which will resist the flow of liquid out of this first container; placing the first container inside a collection vessel which can collect eluate from the container; placing the container and the vessel into a heating block and subsequently having liquid transferred from the container to the vessel.

FIG. 1b, as for 1a, but with the container containing a solid phase material that preferably binds to NAAT-inhibitors rather than nucleic acid. The nucleic acid solution is found in the vessel post Heat-Elution.

FIG. 1c, as for 1b but the solid phase material and sample are mixed prior to being added to the container.

FIG. 1d, as for 1a, but with the container containing a solid phase material that preferably binds to nucleic acids rather than NAAT-inhibitors. The nucleic acid will be immobilised on the solid phase material post Heat-Elution within the first vessel.

FIG. 1e, as for 1d, but the solid phase material and sample are mixed prior to being added to the first vessel.

FIG. 1f, as for 1b or 1c, but the eluted nucleic acid is subsequently concentrated using a different solid phase material which preferably binds to nucleic acid. In this case, the solid phase material consists of paramagnetic beads which can be sedimented from a sample using a magnet. Nucleic acids may be released from the material with a suitable elution buffer, else, the beads can be added directly to a NAAT-based assay.

FIG. 2

Figure 3:
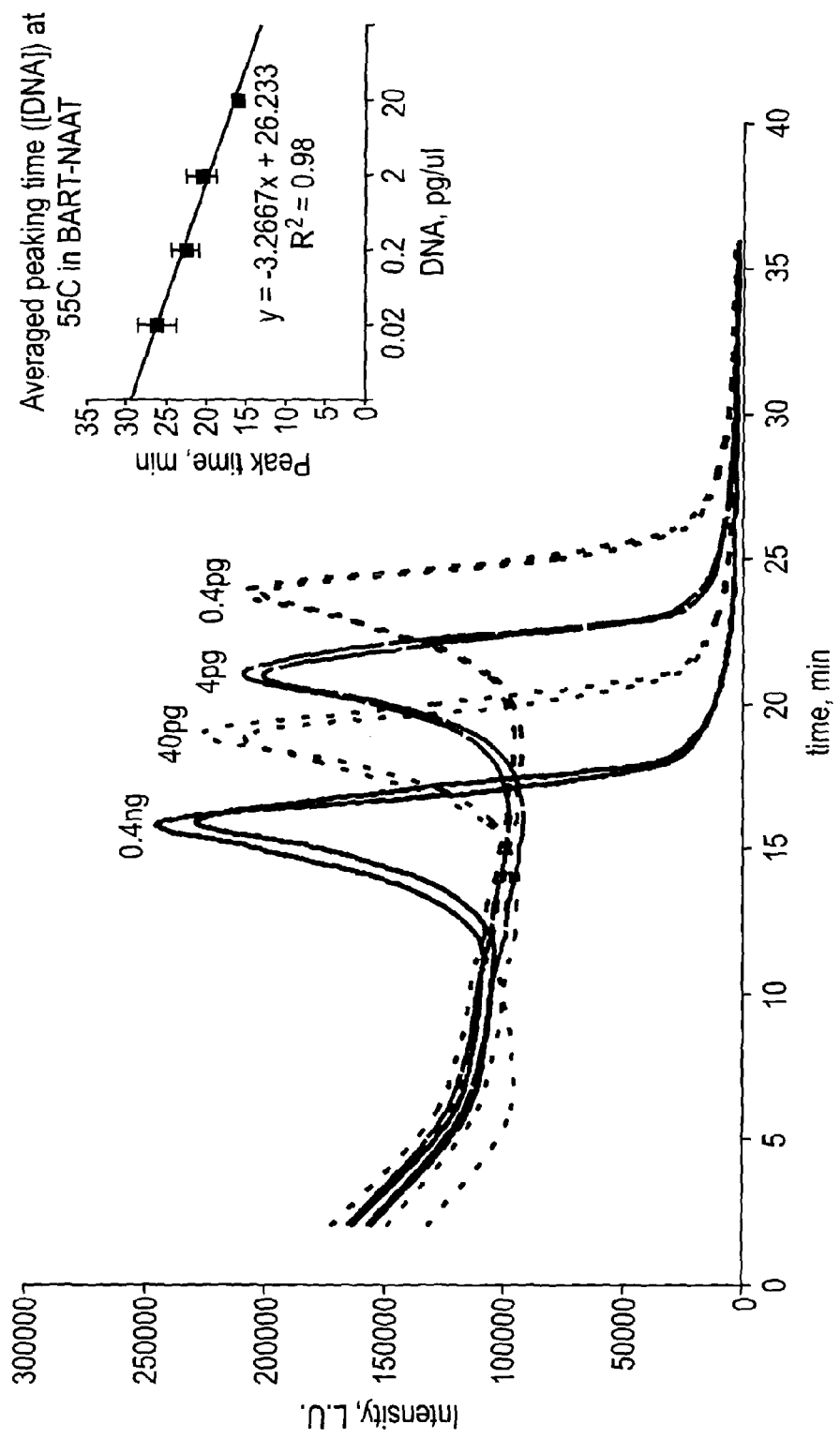

Data showing heat-elution between two vessels plus and minus a solid phase material in the first vessel as described in Example 1.

FIG. 3

Showing typical BART-LAMP outputs for a dilution series of target nucleic acid. Using the BART technology, positive samples give an increase and then decrease in light intensity over time. The time to reach the light peak is inversely proportional to the amount of the targeted nucleic acid present in the amplification reaction.

FIG. 4

Comparison of Heated and Unheated IM-SDVB for inhibitor removal from ISO chocolate enrichment.

FIG. 5

Use of 4° SDVB and 3° SDVB to remove NAAT-inhibition from Coffee Enrichment. Compared to using no resin or the resin IM-SDVB (a), the resins 4° SDVB (b) and 3° SDVB (c) are shown to be extremely effective at removing inhibition caused by instant coffee.

FIG. 6

Humic acid inhibition removal by the resin mixture with heating time on the hot block at 100° C. (a); Temperature profile with time of the heated resin mixture on the hot block at 100° C. (b).

FIG. 7

Temperature profile with time of the Heat-Elution eluate from a hot block set at 100° C.

FIG. 8

Removal of Xylan inhibition by Heat-Elution vs. dilution in buffer only.

FIG. 9

Modulation of elution times by use of differing Frits and the use of wax.

FIG. 10

Amplification profile for *C. difficile* LAMP-BART reactions showing comparison between a *C. difficile* positive faecal sample extracted by A) Heat-Elution of a faecal IM SDVB-buffer mixture through a PVPP column, B) Spun elution of a PVPP column loaded with boiled faecal IM SDVB-buffer mixture and C) Spin clarification of a boiled faecal IM SDVB-buffer mixture.

FIG. 11

Intensity profile of UV visualised intercalator stained 1% agarose showing a Heat-Elution faecal extract and a centrifugally eluted faecal extract.

FIG. 12

Amplification profile for *C. difficile* LAMP-BART reactions showing following extraction of a *C. difficile* positive faecal sample and a *C. difficile* negative sample using Heat-Elution of a proprietary resin mix in a Pierce 8 ml column and a collection tube.

FIG. 13

(a) *C. difficile* LAMP BART detection from *C. difficile* positive clinical stool samples by Heat-Elution against dilutive methods;

(b) Inhibitor Control LAMP BART profile from *C. difficile* positive clinical stool samples by Heat-Elution against dilutive methods

FIG. 14

Comparison of *C difficile* genomic DNA detection pre and post concentration by a simplified Charge Switch® magnetic bead method.

FIG. 15

Integration of multi-vessel sample preparation & amplification using heat-elution

FIG. 16

Comparison of *C difficile* genomic DNA detection with and without performing Heat-Elution with Charge Switch® magnetic beads incorporated into the first vessel.

EXAMPLES

Example 1: Heat is Sufficient to Drive Eluate from a Container Against a Resistive Force Using Standard Plastic Consumables and Solid-Phase Matrices Demonstrating the Heat-Elution Principle The heat within the sample preparation column permits a build up of pressure that allows self elution of the sample lysate through the column base, and does not require assistance of a centrifuge or syringe to achieve this (FIG. 1). This feature is exemplified in a (a) small 0.8 ml column scale as well as a (b) larger 8 ml column.

(a) A 0.8 ml column (Pierce #89688) was filled with a proprietary resin mixture in reaction buffer to a final volume of 600 µl where the excluded buffer volume was 327.5 µl. The cap was closed tightly and the twist tab was broken off. The column was placed into a 2 ml collection tube and the entire column and tube was placed onto a heating block at 95° C. for 10 min. During this time pressure had built up within the column and the majority of the liquid was gradually driven out through the base of the column into the collection tube.

(b) An 8 ml column (Pierce #89897) was filled with a proprietary resin mixture in reaction buffer to a final volume of 3.4 ml where the excluded buffer volume was 1.96 ml. The cap was closed tightly and the twist tab was broken off. The column was placed into a 13.5 mm internal diameter collection tube (Fisher #FB51579) and the entire column and tube was placed onto a bespoke heating block that has an insert depth of 80 mm. This was heated at 100° C. for 10 min. During this time pressure had built up within the column and the entire eluate was gradually driven out through the base of the column into the collection tube.

To confirm that moderate heat can elute liquid phase via the Heat-Elution method in the present of a solid phase and solid-phase filter which creates back-pressure resisting elution a solution was eluted in the presence of Chelex 100 (Bio-Rad). Specifically, A 10% suspension of Chelex 100 in molecular grade water was made as follows: 1.096 g of Chelex was place in a 50 ml beaker and 10.96 ml of molecular grade water (Sigma) added. This was stirred on a magnetic stirrer following addition of a small flea. 800 µl was added to two pre-weighed Pierce 89868 columns with their snap tabs already removed. These columns were placed in a 2 ml collection tube and centrifuged at 8000 rpm for 1 minute to remove the water from the Chelex resin in the column. 250 µl of molecular grade water was added to these two columns and two other pre-weighed columns. These were placed into pre-weighed 2 ml snap cap tubes and placed on a 100° C. heat block or kept at room temperature for 5 minutes. At the end of the 5 minutes columns and eluate tubes were weighed to determine the volume of eluate and the volume of water left on the column. Neither of the columns held only at room temperature eluted any water, whereas, both the heated columns had eluted with 198.5 µl eluted from the heated Chelex column and 226.4 µl from the water only column (FIG. 2).

Example 2: The BART Reporter System

The BART reporter system has been explained in detail in WO2004/062338 and WO2006/010948, which are hereby incorporated by reference. BART is an example of a reporter system designed for isothermal NAATs which gives a single type of signal from a sample, a bioluminescent signal. BART utilises the firefly luciferase-dependent detection of inorganic pyrophosphate. This is produced in large quantities when 'target' sequences are detected using a NAAT. As such, molecular diagnostics can be achieved with BART simply by measuring the light emitted from closed tubes, in a homogeneous phase assay (FIG. 3). BART is proven with several different NAATs, operating between 50-63° C. The BART reporter is a particularly effective means to follow the rate of amplification of a NAAT since the light output represents a measure of the instantaneous rate of amplification (whereas e.g. fluorescent outputs show the accumulation of a signal and hence the measurements have to be differentiated to obtain the amplification rates).

Example 3: Solid Phase Materials which Remove NAAT Inhibitors Perform Better when they are Eluted at Higher Temperature (which Naturally Happens with Heat-Elution)

i) Ability of the Solid Phase Resin "3° SDVB" to Remove NAAT-Inhibitors at Different Temperatures 20 µl of a 187.5 ng/µl humic acid stock was added to BART-LAMP reaction buffer (190 mM Bicine, pH8.0) in two sets containing either 580 µl of buffer with no 3° SDVB resin or 580 µl of buffer with 3° SDVB at 20%. One set was vortex mixed, then heated at 95° C. for 5 minutes followed by a second vortex. The control set was vortexed and left at room temperature for this time then vortexed again. 20 µl of each supernatant was used to reconstitute a freeze dried BART-LAMP reaction containing a fixed number ($10^4$) of a particular target DNA molecule (referred to herein as the 'Inhibitor control'). The peak times of duplicate reactions were subsequently compared. The presence of inhibitors may either slow or abolish amplification, in which case the peak times (the time it takes the BART reporter system to give the characteristic light peak) will increase or disappear altogether respectively. This showed that with no heat and no resin the reaction times with humic acid were 59.7±0 min. These improved to 57.0±0.5 min in the presence of resin and further significantly improved with the heated resin to 38.4±2.1 min.

ii) Ability of the Solid Phase Resin "IM-SDVB" to Remove Complex NAAT-Inhibitors at Different Temperatures.

Figure 4:
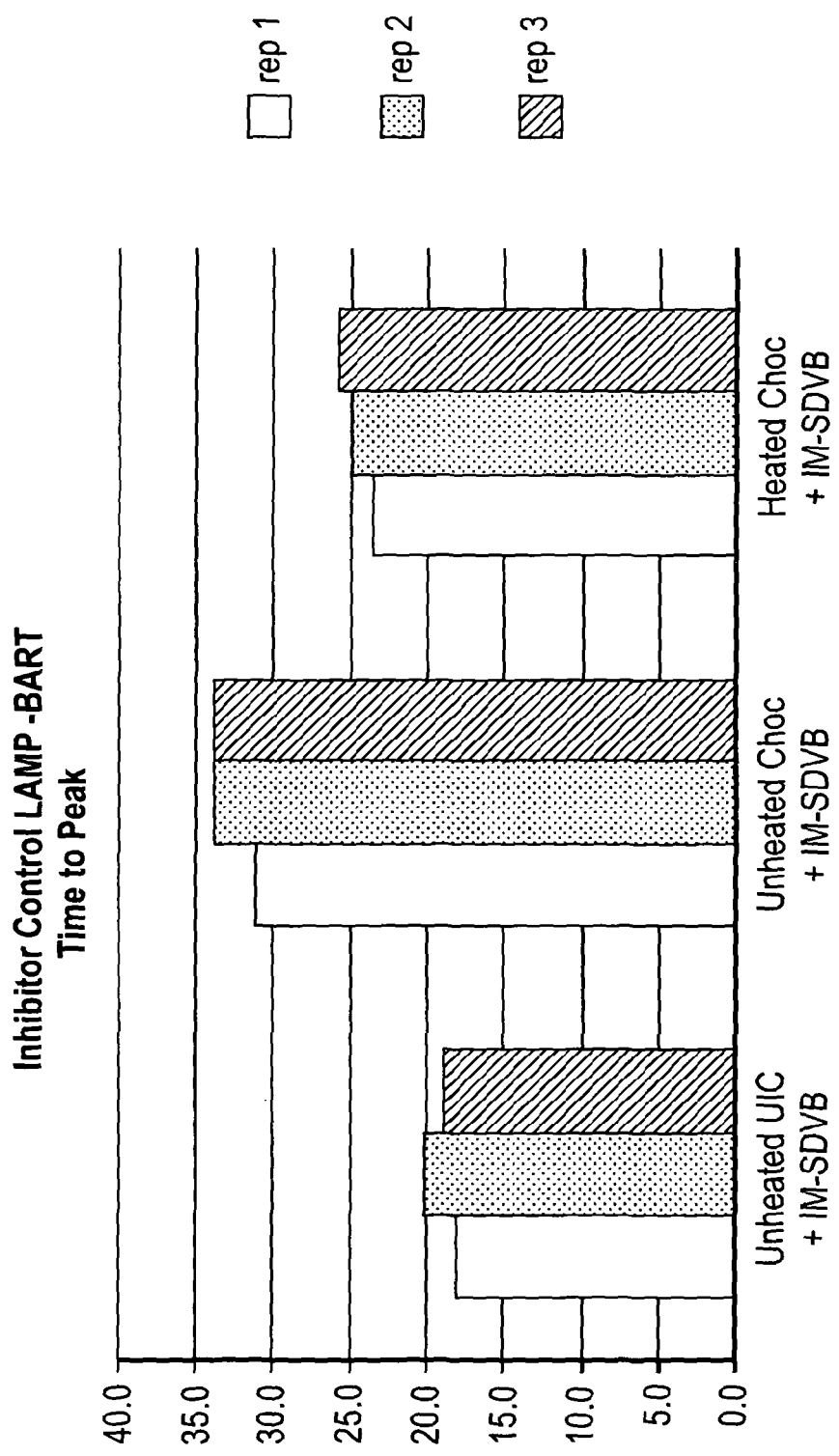

The process of testing chocolate for food pathogens involves incubating 25 g of chocolate in 250 ml of an enrichment broth containing buffered peptone water with milk powder and the dye Brilliant Green. Following incubation it had been found that this enrichment broth was highly inhibitory to NAATs; this broths is referred to herein as ISO chocolate enrichment. The identity of the inhibitor(s) is unknown. Two sets of 20 µl samples of an ISO chocolate enrichment were added to 580 µl of 20 mM Tris buffer pH 8.8 containing 10 mM ammonium sulphate, 0.15% Triton X-100, 0.4 mg/ml polyvinylpyrrolidone and 0.09% sodium azide with 10% (w/v) IM-SDVB (a cation exchange resin consisting of a styrene divinylbenzene copolymer with iminodiacetate functionalised groups.) in 1.5 ml centrifuge tubes. These were pulse vortexed. One set of chocolate sample tubes were heated at 110° C. on a heating block for 5 minutes. The other set was kept at room temperature for the same time. After 5 minutes both sets of tubes were pulse vortexed, allowed to cool and 20 µl from each tube used to reconstitute freeze dried inhibitor control BART-LAMP reactions in triplicate in 200 µl PCR strips. FIG. 4 shows that the heated chocolate enrichment gave a mean peak time of 24.7±1.15 min, which is 8.1 min faster than the unheated mean peak time of 32.8±1.61 min. Blank inhibitor control ran simultaneously gave a peak time of 18.9±1.00 min. Therefore, heating the chocolate in IM-SDVB resulted in a reduction of inhibition of BART-LAMP compared to not heating.

iii) Ability of the Solid Phase Resin "PVPP" to Remove the NAAT-Inhibitor Humic Acid at Different Temperatures.

200 µl of PVPP suspension was pipetted to 200 µl tubes that were spun down to give a dense PVPP bed and 100 µl of the excess liquid removed. 100 µl of 1.25 µg/µl humic acid was added to the top of the PVPP bed. The addition was vortex mixed throughout the PVPP. Three tubes were heated at 95° C. for 15 minutes and three tubes were left at room temperature for 15 minutes. All tubes were vortexed after 5 minutes and put back to temperature. 20 µl was taken to a separate PCR tubes and particulates were spun down. Some of the room temperature humic acid over PVPP supernatant was also heated at 95° C. for 15 min. 5 µl from each was added to 15 µl Inhibitor Control BART-LAMP reactions Inhibitor control peak times for humic acid on PVPP heated at 95° C., humic acid on PVPP at room temperature and the supernatant from the latter heated at 95° C. were 32.85±7.20 mins, 47.63±8.17 mins and 59.16±14.92 mins, respectively. This showed that heated PVPP removed more humic acid inhibitor than room temperature PVPP and that heating the humic acid supernatant from the room temperature PVPP extract gave no additional inhibition relief. In this study uninhibited peaks with water were at 23.11±3.31 mins.

iv) Ability of the Solid Phase Resins "4° SDVB" and "3° SDVB" to Remove Complex NAAT-Inhibitors at Different Temperatures.

Instant coffee can be demonstrated to contain potent NAAT inhibitors, therefore instant coffee represents a useful inhibitor model. Instant coffee (1 g) was added to 10 ml of buffered peptone water and incubated at 37° C. for 18 hours. 20 µl of the enrichment was added to tubes of 580 µl BART-LAMP amplification buffer containing no resin, 10% IM-SDVB, 300 µl of 4° SDVB (a macroporous strong base anion exchange resin consisting of a styrene divinylbenzene matrix with quaternary amine functionalised groups) or 300 µl of 3° SDVB (a macroporous styrene divinylbenzene copolymer with tertiary amine functionalised groups). All tubes were vortexed and heated at 110° C. for 5 min. Heated tubes were pulse vortexed and allowed to cool. 20 µl was added in duplicate for each condition to reconstitute freeze dried inhibitor control BART-LAMP reactions in triplicate in 200 µl PCR strips. Coffee enrichment in buffer without resin, with IM-SDVB (FIG. 5a), 4° SDVB (FIG. 5b) and 3° SDVB (FIG. 5c) gave an average peak times of 45.3±8.3 min, 37.8±3.8 min, 19.7±0.8 min and 22.4±1.5 min, respectively. Thus, both 4° SDVB and 3° SDVB have removed inhibitors from the coffee enrichment permitting inhibitor control peaking no more than 6 min slower than a water inhibitor control peak time of 17.1±0.0 min, compared to a 28 min delay for the coffee enrichment in buffer alone.

v) Temperature Dependence of Inhibitor Removal

Figure 6B:
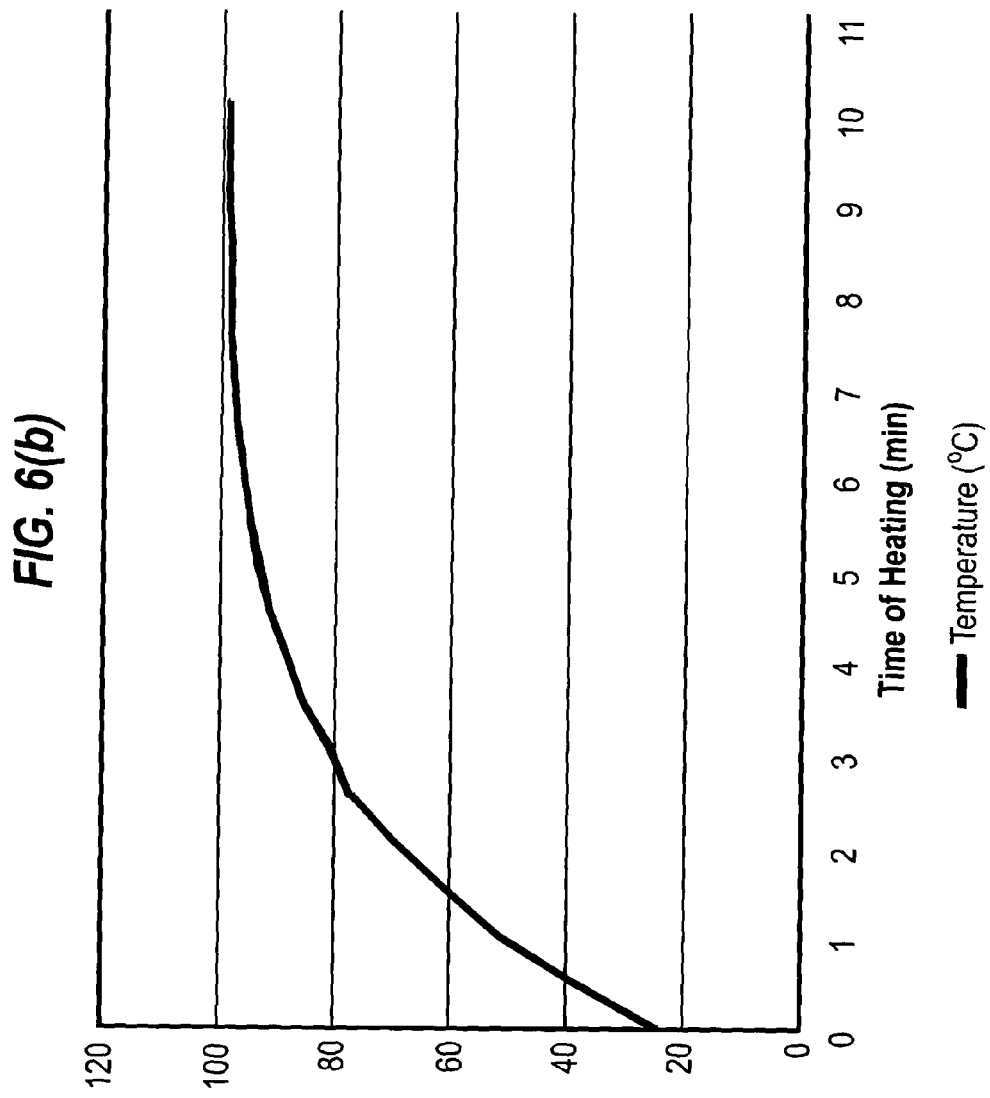

Nine 2 ml tubes were filled with a particular resin mixture (10% v/v Chelex 100, 25% v/v Optipore SD-2 and 25% v/v Diaion WA30) in BART-LAMP reaction buffer where the excluded buffer volume was 633.2 Into each of these 21.8 µl of a 187.5 ng/µl stock of humic acid were added and vortex mixed. Each tube was placed on a heating block at 100° C. for time points 0, 1, 2, 3, 4, 5, 8 and 10 min, after which they were each removed from the heating block, then immediately vortexed and 200 µl of the supernatant removed from the resins. The temperature in another tube was also monitored every 30 sec with a thermocouple throughout the 10 min heating. Two further controls were setup of 655 µl buffer only (no inhibitor control) and 21.8 µl humic acid in 633.3 µl (inhibited control). These were heated on the hot block for 10 min. The supernatants from each were used to reconstitute freeze dried Inhibitor Control LAMP-BART reaction mixes in duplicate. These were run at 60° C. and the peak times of the reactions compared during the time course. Data in FIG. 6a showed that there was a trend of increased inhibitor removal with increased heating time, and with FIG. 6b this correlated to the temperature increase. By 5 min heating it was demonstrated that maximal inhibition relief was achieved, where the recorded temperature of the resin formulation reached 93.4° C. The inhibitor control peak time reduced from 43.2±0.5 min at 0 min incubation to 19.7±0.5 min after 10 min heating.

A set of tubes with the proprietary resin mixture and humic acid was also prepared as unheated controls and incubated at room temperature. After time points 0, 1, 2, 3, 4, 5, 8 and 10 min, they were each immediately vortexed and 200 µl of the supernatant removed from the resins. The supernatants from each were used to reconstitute freeze dried Inhibitor Control LAMP-BART reaction mixes in duplicate. These were run at 60° C. and the peak times of the reactions compared during the time course. The measured temperature of the resins by a thermocouple was 22.7° C. In these tubes the inhibitor control peak time at 0 min incubation was 49.0±1.0 min. Even after 10 min incubation the peak time was 44.2±2.7 min showing no significant reduction in inhibition with unheated resins, and confirming that heated resins were more effective in inhibitor removal.

vi) Temperature Kinetics of Heat-Elution

Figure 7:
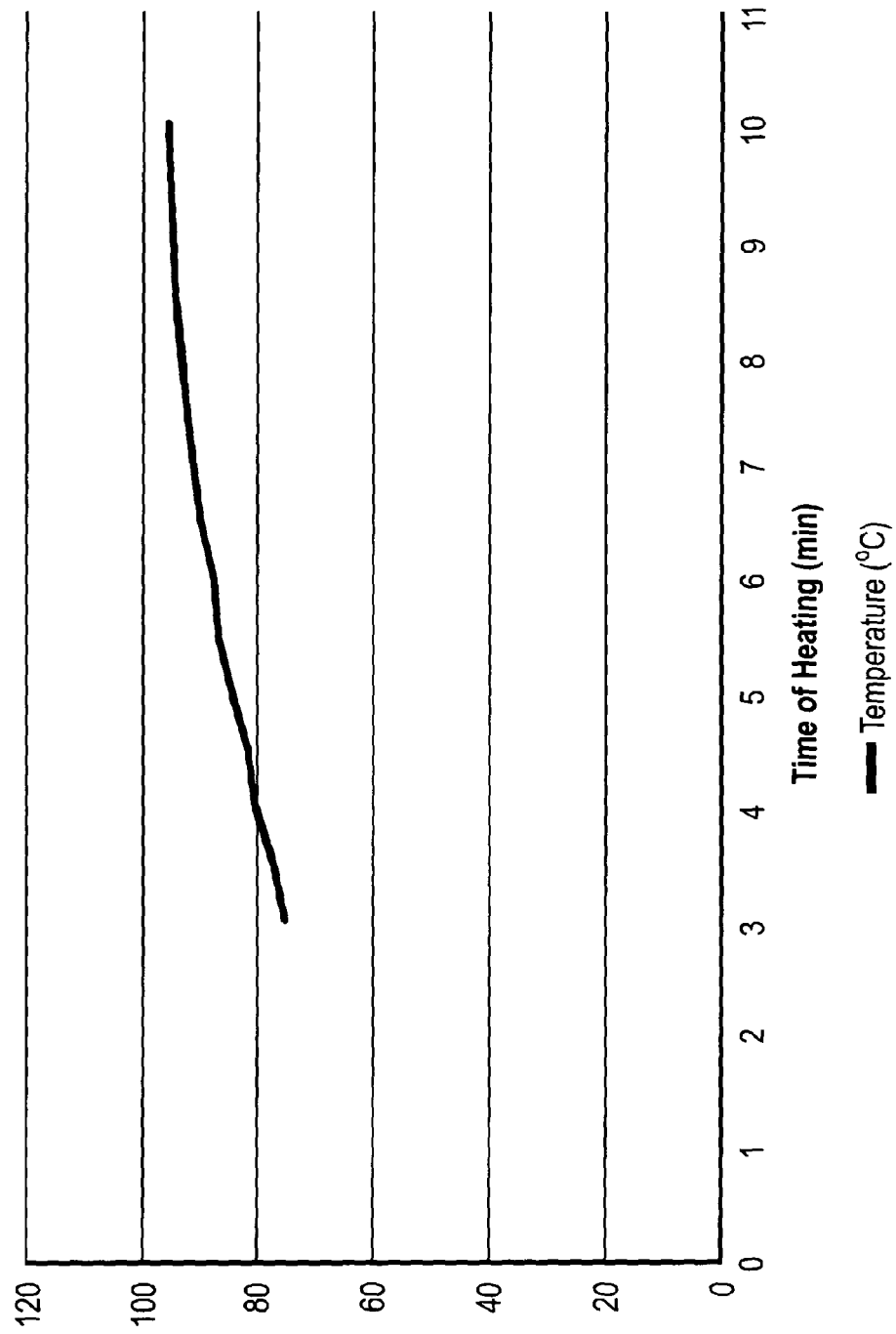

An 8 ml column (Pierce #89897) was filled with a particular resin mixture ((10% v/v Chelex 100, 25% v/v Optipore SD-2 and 25% v/v Diaion WA30) in BART-LAMP reaction buffer where the excluded buffer volume was 1.965 ml. The twist tab was broken off and the thermocouple was placed into the elution tip. The column was then placed into a 13.5 mm internal diameter collection tube (Fisher #FB51579) and the entire column and tube was placed onto a bespoke heating block that has an insert depth of 80 mm. This was heated at 100° C. and the temperature of the eluate monitored after 3 min, from when elution begins, every 30 sec for 10 min. It was confirmed that the optimal temperature correlating to maximal inhibitor removal (FIGS. 6a and 6b) was easily achieved during the heating time frame. FIG. 7 shows that an 8 min heating time allowed a rise in eluate temperature to >93° C. In fact since temperature is related to inhibitor removal then significant inhibitor removal would be occurring by 76° C. which translates into at least 3 min heating in this format.

vii) Removal of Sample Eluate from Hot Resin Showed Better Inhibitor Removal than from Cold, in a Heat and Mixing Study.

A 1 in 5 dilution of a an extract from a stool sample, which had been characterised as containing an abundance of NAAT inhibitors, was made in LAMP-BART reaction buffer. 50 µl (10 mg) was mixed with 655 µl buffer only as a 'no resin' control. Further 50 µl amounts were added to six tubes containing a proprietary resin cocktail of which the excluded volume of buffer was also 655 µl. Each was heated at 95° C. for 10 min. Tubes were either (a) mixed both pre and post heating; (b) not mixed; (c) mixed before heating; (d) mixed after heating; (e) pre and post heat mixed and hot supernatant removed before cooling; (f) pre heat mixed and allowed to cool after heating then mixed. 20 µl of each supernatant was used to reconstitute freeze dried Inhibitor control LAMP-BART reaction mixes in duplicate and run at 60° C. The peak times of the reactions were compared. Without resins, detection was not possible in the 120 min run time. With (b) and (c) there was also no detection indicating the initial mix with cold resin had no inhibitor binding effect. Reactions of (a), (d) and (e) all showed detection within 22.4 to 28.8 min where effective inhibitor removal occurred showing the immediate post heat mixing with hot resin was essential for inhibitor removal. If sample and resins were cooled to room temperature and mixed (f) then detection also failed within 120 min.

Example 4: Use of the Heat-Elution Method to Remove Inhibitors from Samples i) Heat-Elution can be Used to Remove the NAAT-Inhibitor Xylan 27.3 µl of a 60 µg/µl Xylan stock was added to 655 µl of reaction buffer and heated on a heating block at 100° C. for 6 min. 81.8 µl of a 60 µg/µl Xylan stock was added to a column containing a proprietary resin mixture with an excluded volume of 1.965 ml. The cap was closed tightly and the twist tab was broken off. The column was placed into a 13.5 mm internal diameter collection tube (Fisher #FB51579) and the column and tube was placed into a conical flask of boiling water for 6 min.

Figure 8:
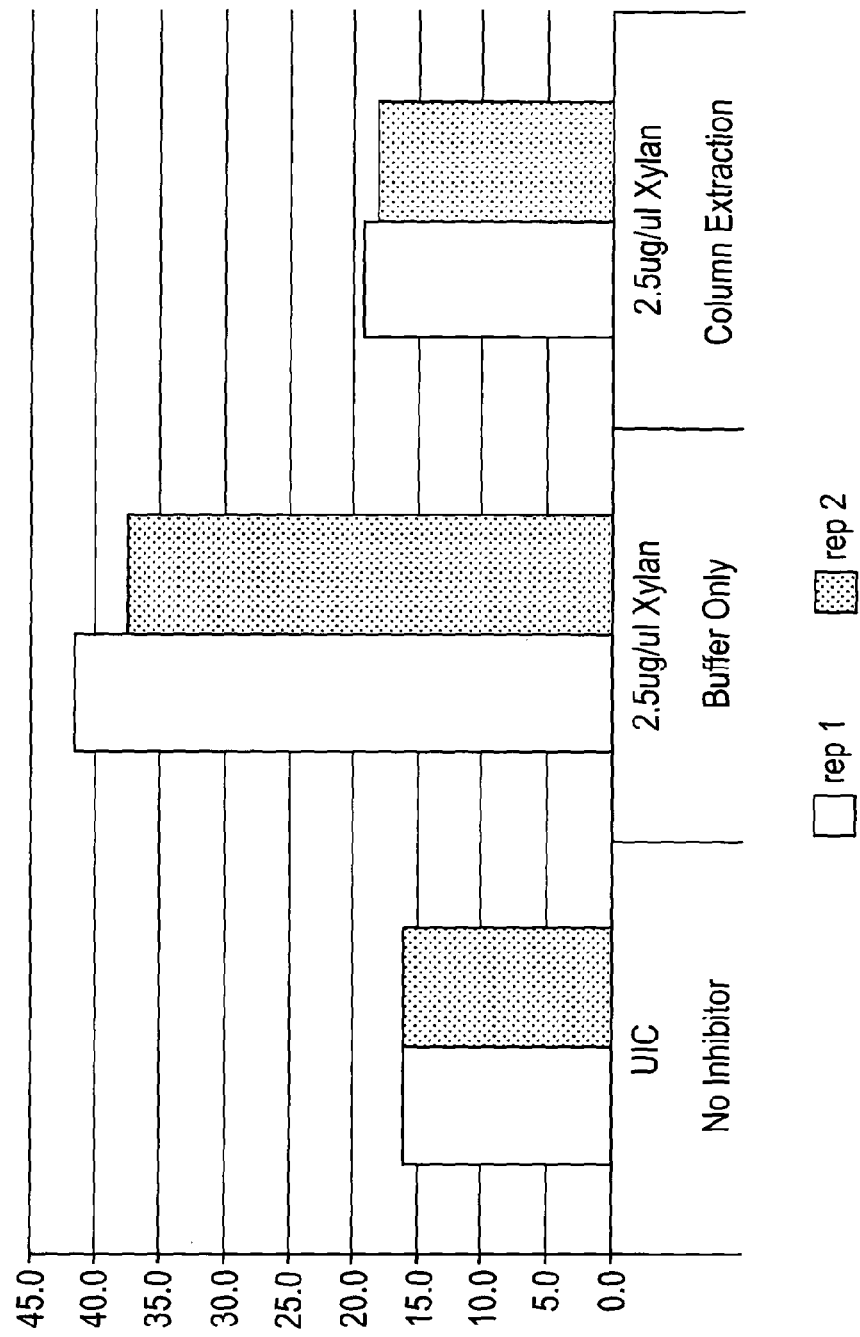

The eluates from each were used to reconstitute freeze dried Inhibitor control BART-LAMP reaction mixes in duplicate. These were run at 60° C. and the peak times of the reactions compared. FIG. 8 shows that without resin treatment the detection times were 39.5±2.1 min in the presence of xylan. However the column elutes gave detection times of 18.7±0.6 min indicating xylan inhibitor removal by the resins at the same dilution factor.

Example 5: Control of Elution i) Small Pore Sized Frits and High Melting Temperature Paraffin Wax Used to Modulate Elution For efficient sample inhibitor removal it was necessary that the sample was exposed to heated resins for a sufficiency of time before elution of the liquid phase. As such, it is necessary to control the rate of elution by some means.

Elution rate was modulated by the use of a small pore sized polyethylene frit and a high melting temperature wax beneath the resins to constrict eluate flow out of the column. The start of elution during the heating was delayed by 3 min and complete before 10 min to ensure sufficient exposure of sample to heated resins, (FIG. 9).

Figure 10:
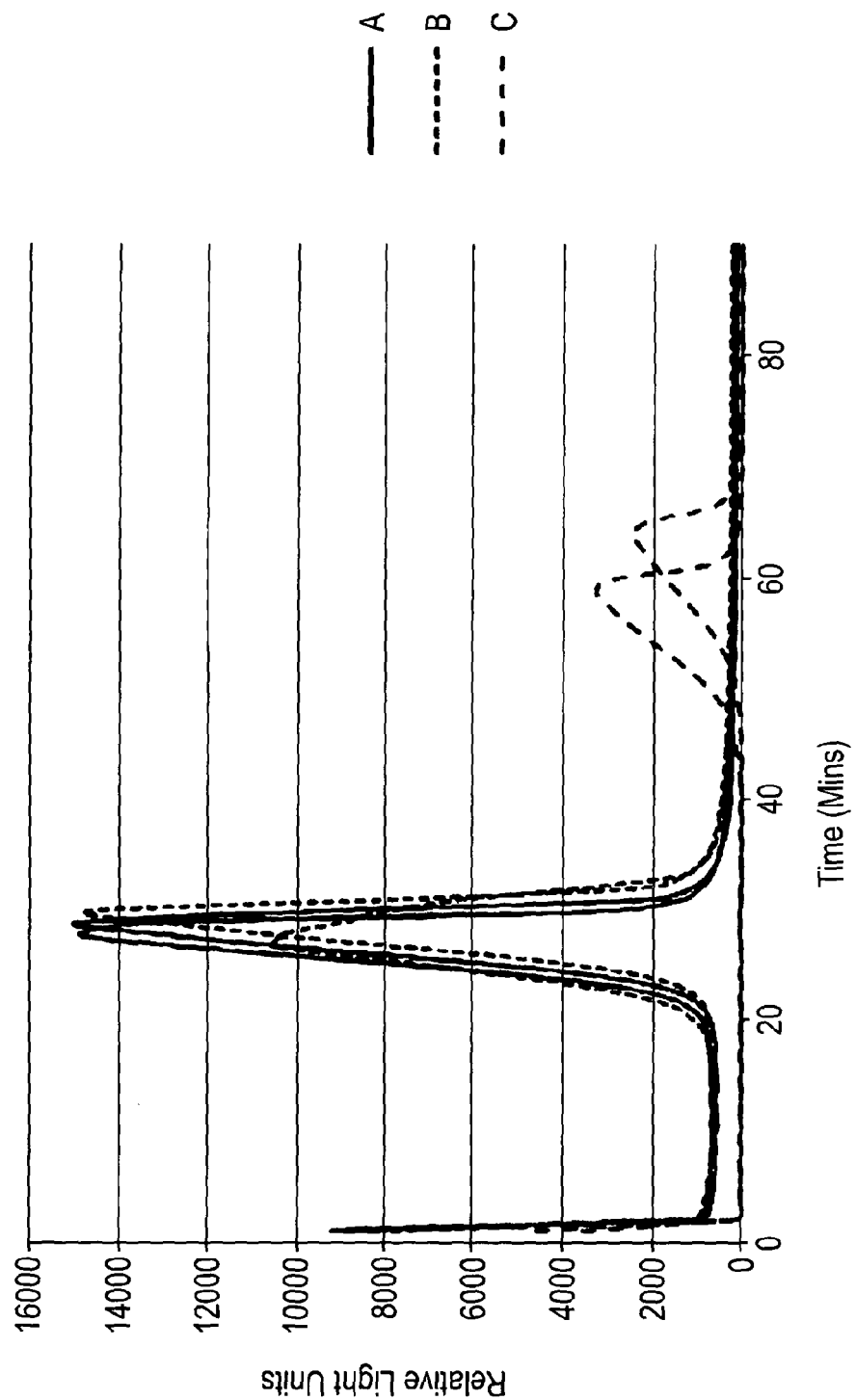

Example 6: Quality of Eluted Nucleic Acids with Heat-Elution i) Heat-Elution can be Better than Centrifugation for Inhibitor Removal: Comparison Between Spun Elution and Heat Pressure Elution of a Faecal Extract by LAMP-BART 20% IM-SDVB in 27 mM dithiothreitol and 13.3 mM BICINE pH 5 was added to 250 µl of a C. difficile positive diarrheal sample and vortex mixed. 200 µl volumes of this vortex homogeneous mixture were added to an 800 µl spin column containing a compact bed of PVPP or to two 1.5 ml tubes. The PVPP column containing the faecal-IM SDVB-DTT-BICINE mixture was capped tightly, the plastic tab at the bottom of the column removed to open the base of the column, placed in a 1.5 ml collection tube and heated on a hot block for 15 min at 105° C. (A). This resulted in eluate being Heat-Elution into the collection tube. The 1.5 ml tubes containing sample were simultaneously heated for 15 min at 105° C. When cooled, tubes were centrifuged at 14,000 rpm for 5 min and the supernatant from one of the tubes transferred to a bottom opened 800 µl spin column containing a compact bed of PVPP in a 1.5 ml collection tube. This PVPP column was eluted by centrifugation at 8,000 rpm for 2 min on a microcentrifuge (B). The extract from the other 1.5 ml tube was used without PVPP column (C). 5 µl volumes from each extract were added in duplicate to 15 µl reaction volumes of C. difficile LAMP-BART reagents in the tubes of a PCR plate. These were covered with oil and placed on BART amplification detection instrument at 60° C. FIG. 10 shows the peak times for the faecal sample directly lysed in the PVPP column was 28.28±0.75 min, heat lysis in the tube and spinning on PVPP column was 28.28±2.26 min and heat lysing the faecal sample in buffer and spinning down the solids gave 61.39±3.78 min. Thus, for this particular faecal sample, heat lysing the sample and heat pressure elution within a PVPP column was as good as lysing the sample in a tube and then spin eluting the lysate on a PVPP column. The spun lysate gave slower detection due to the inhibitors still present in the lysate.

ii) Heat-Elution Facilitates Elution of High Molecular Weight DNA

Figure 11:
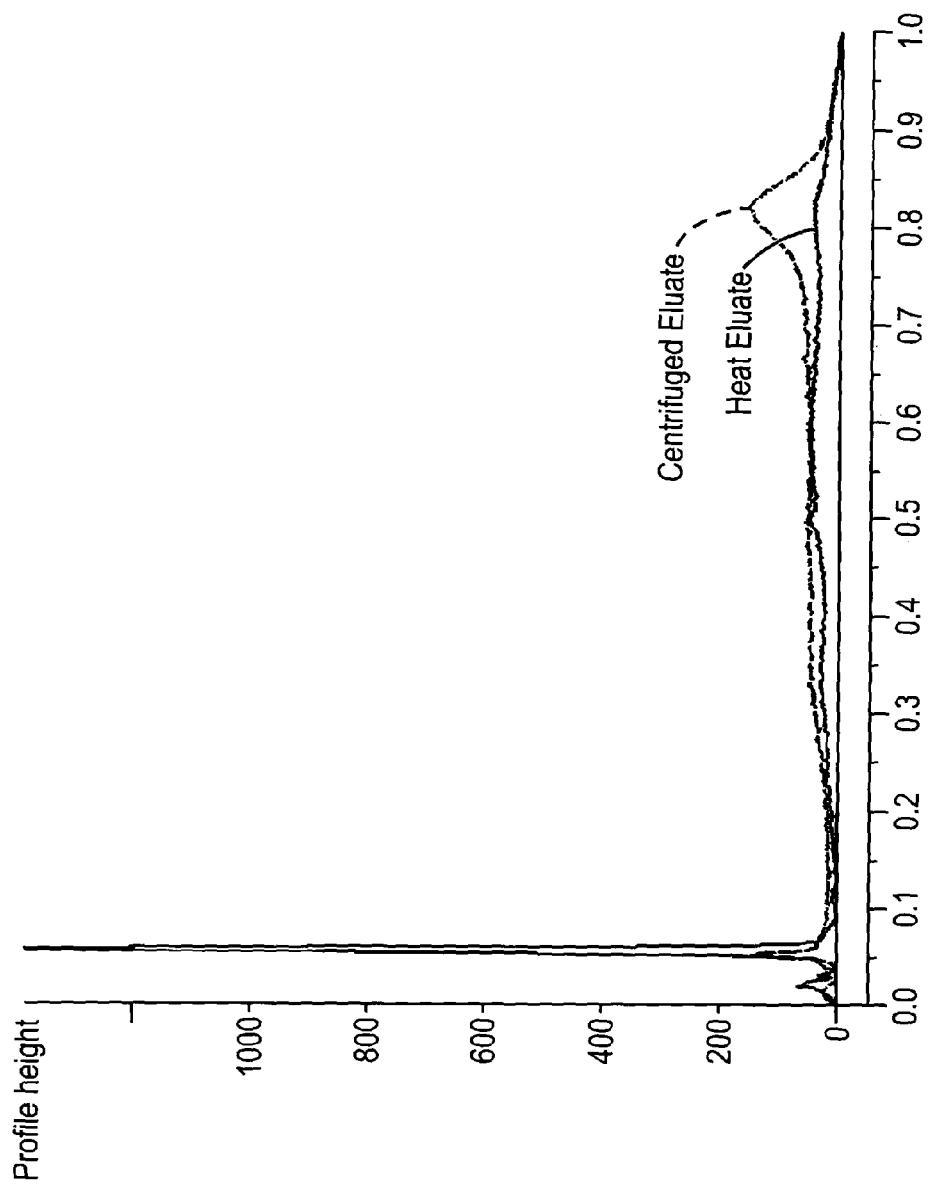

A 0.8 ml column (Pierce #89688) was filled with a proprietary resin to a final dry volume of 555 µl open for elution in a 1.5 ml tube. 333 µl of a faecal sample was added to another tube containing 20% IM-SDVB in buffer and mixed by vortexing. 200 µl of this mixture was added to the 0.8 ml column, tightly capped and then heat eluted sitting in its 1.5 ml tube on a 95° C. hot block for 15 minutes. Following elution, the tube was allowed to cool and the column transferred to a fresh tube and centrifuged at 8,000×g for 3 min. 15 µl of both heat and spun eluates were ran on a 1% agarose gel containing an intercalating stain after mixing with 3 µl of loading buffer, and a gel image captured on a transilluminator (FIG. 11). The intensity profile of heat eluate shows that the stained DNA is substantially high molecular weight that remains in the well of the gel. Subsequent centrifugal elution of the same column shows additional low molecular weight staining. Centrifugation is known to cause shearing of high molecular weight DNA that results in low molecular weight fragments and can affect low copy number detection through the breakage within the target site for amplification. The absence of DNA shearing is advantage of heat pressure extraction elution.

Figure 12:
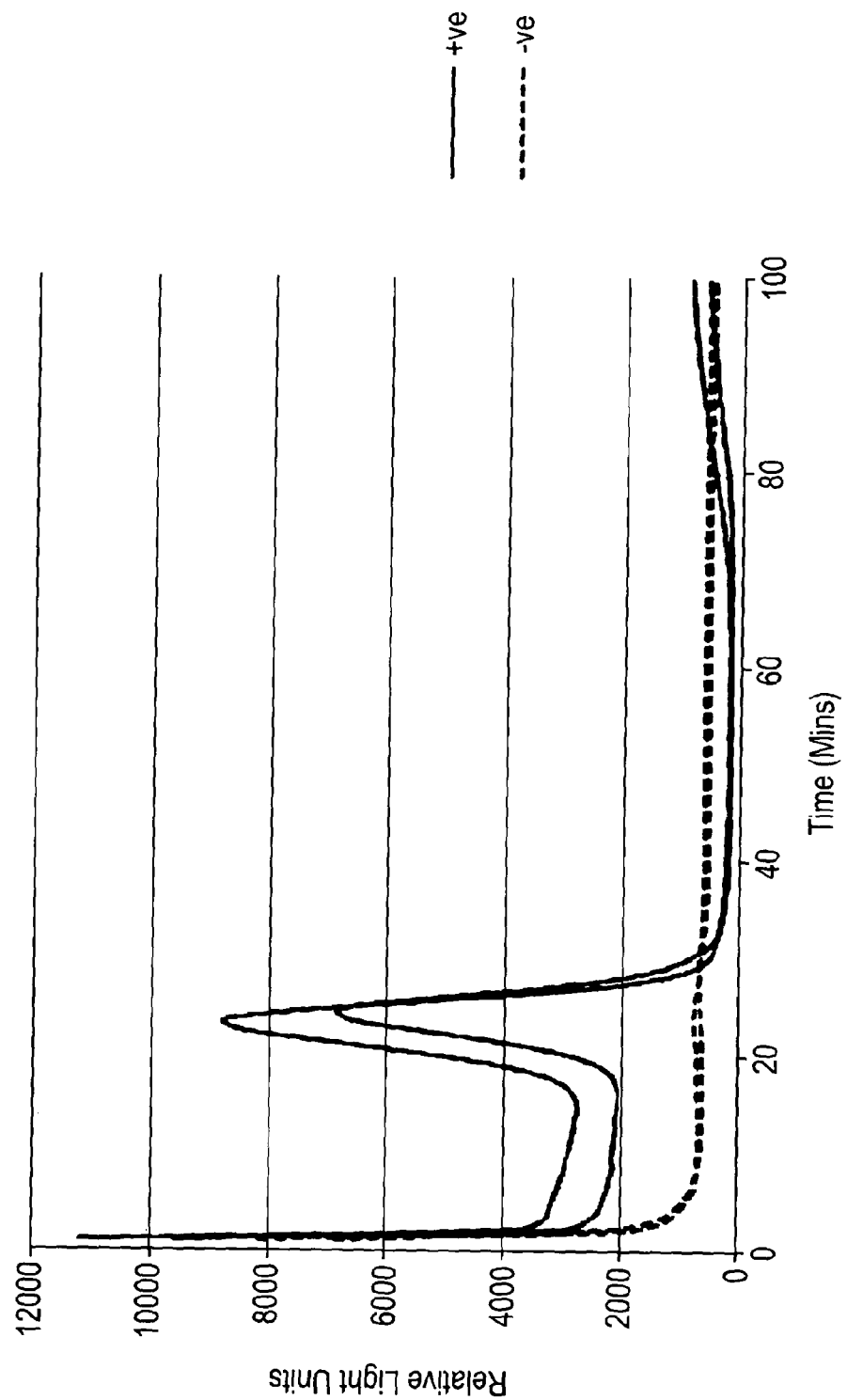

Example 7: Demonstration of Heat-Elution Principle i) Use for Detection of *C. difficile* Following Extraction of Stool Samples 8 ml columns (Pierce #89897) were filled with a proprietary resin mixture in reaction buffer to a final volume of 3.4 ml where the excluded buffer volume was 1.965 ml. One sample each for *C. difficile* positive and negative faecal sample was sampled using a sterile micro ultrafine flocked swab (Puritan #25-3318 1PN 50). The end of the swab was mixed within the resin mixture, the stem of the swab snapped of and the column tightly closed. The twist tab was broken off and the column was placed into a 13.5 mm internal diameter collection tube (Fisher #FB51579) and the entire column and tube was placed onto a bespoke heating block that has an insert depth of 80 mm. This was heated at 100° C. for 10 min. During this time pressure had built up within the column and the entire eluate was gradually driven out through the base of the column into the collection tube. The eluates from each were used to reconstitute freeze dried Inhibitor control LAMP-BART reaction mixes in duplicate. These were run at 60° C. and the peak times of the reactions compared. This gave detection time for the *C. difficile* positive sample of 24.04±0.75 min whereas the *C. difficile* negative sample did not peak (FIG. 12), therefore showing that the method allows successful detection of *C. difficile* from stool.

ii) The Heat-Elution Removes Faecal Inhibition without Compromising Detection by Avoiding the Need for Excessive Dilution.

6×8 ml columns (Pierce #89897) were filled with a proprietary resin mixture in reaction buffer where the excluded buffer volumes were 1.965 ml. Six confirmed *C. difficile* positive clinical stool samples were tested by the pressure column elution method. 150 µl of a 1 in 5 dilution of each clinical sample in reaction buffer (30 mg) were added to each column and mixed. The twist tabs were broken off. The columns were then placed into a 13.5 mm internal diameter collection tubes (Fisher #FB51579) and the entire columns and tubes were placed onto a bespoke heating block that had an insert depth of 80 mm. These were heated at 100° C. for 10 min and the eluates cooled to room temperature. 20 µl of the eluates were used to reconstitute freeze dried *C. difficile* and Inhibitor Control LAMP-BART reagent.

Figure 13A:
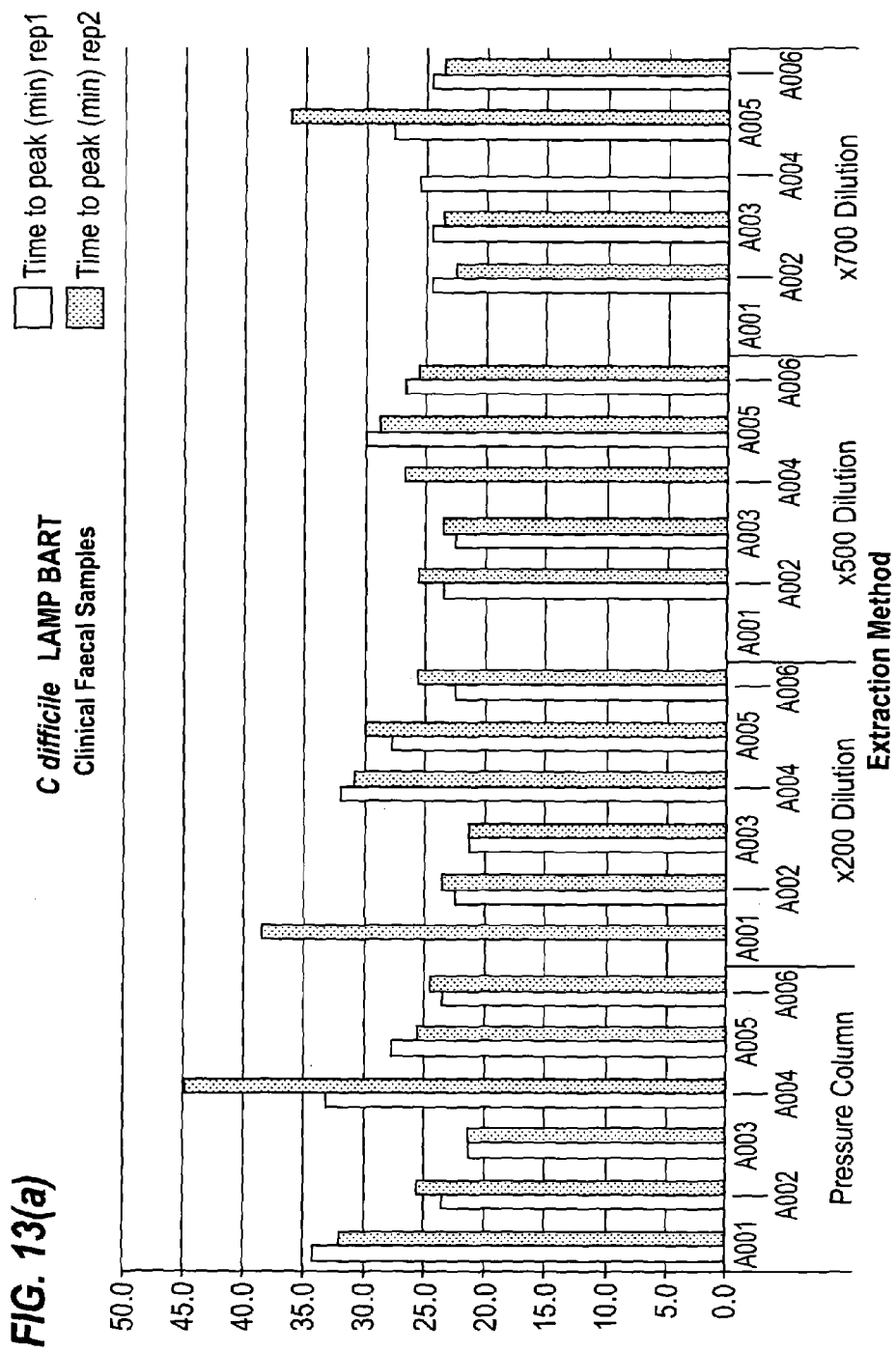

The six stool samples were also diluted to levels in the order of those used in other available commercial *C. difficile* tests. These were prepared in reaction buffer to 1 in 200, 1 in 500 and 1 in 700 in final 600 µl volumes, vortex mixed and heated in 2 ml tubes on a heating block set at 100° C. for 10 min. The tubes were mixed and then 20 µl of the lysates were used to reconstitute freeze dried *C. difficile* and Inhibitor Control LAMP-BART reagent. Reactions were run at 60° C. for 90 min on the BART detection hardware. Samples A001 and A004 had a low *C. difficile* load, confirmed by high Ct values in the PCR method used by the Public Health Laboratory. Extraction by the Pressure Column had permitted detection of all replicates, including these two challenging samples where the dilutive methods between 200× and 700× dilution showed a compromise in detection. *C. difficile* LAMP-BART peak times for the methods are compared in FIG. 13a The Heat-Elution method required no more than 1 in 70 dilution in the resin mixture to sufficiently remove faecal inhibition.

Figure 13B:
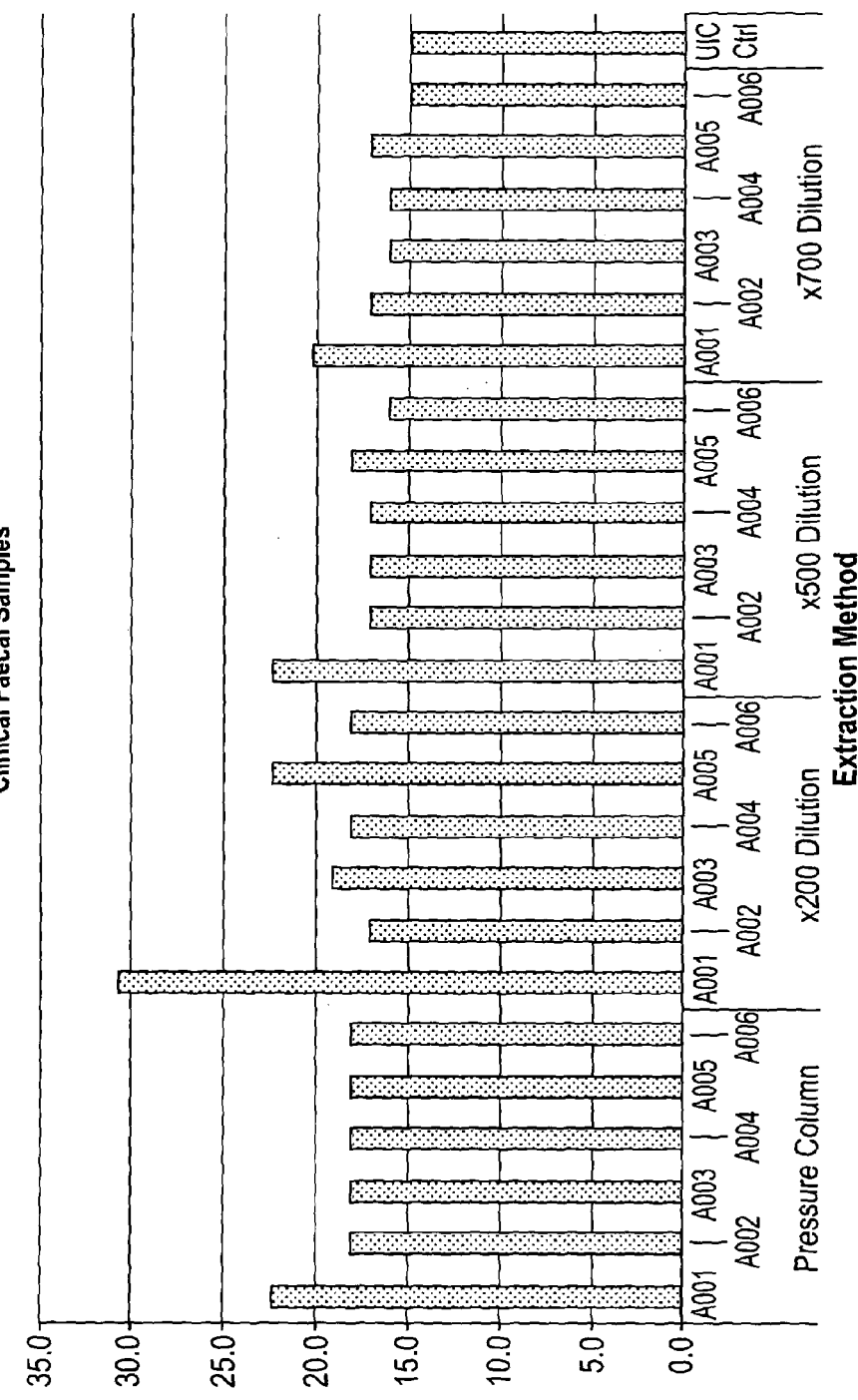

Sample A001 was a solid stool with a high inhibitor load and with the lowest *C. difficile* level in the set. This sample was successfully detected by the Heat-Elution method, where detection at 1 in 200 was compromised and 1 in 500 and 1 in 700 completely failed due to excessive dilution. FIG. 13b shows for this sample, the inhibitor control at 1 in 200 showed more inhibition than the eluate from the column (diluted to 1 in 70). In fact it was necessary to dilute the sample 1 in 500 to alleviate inhibition. In terms of inhibition removal, the Heat-Elution column with the resins was more effective than a 200-fold dilution as seen by the trends of the more inhibitory samples A001 and A005.

iii) Detection of Norovirus Following Heat Pressure Extraction

50 µl of a Norovirus GII-4 positive diarrheal sample was added to 150 µl of 20% IM-SDVB in 20 mM MES, 40 mM DTT in a 1.5 ml screw cap tube. This was mixed, capped and placed on a 95° C. hot block for 10 min and then taken to ice for 2 min and then centrifuged at 17,000 g for 5 min. 100 µl of the supernatant was added to a compacted PVPP bed in an 800 µl tube and spun eluted at 8,000×g for 2 min. 5 µl volumes from the extract was added in duplicate to 15 µl reaction volumes of norovirus GII-4 reverse transcriptase LAMP-BART reagent in the tubes of a PCR plate together with 1 µl of the same faecal sample previously extracted using Boom technology. These were covered with oil and placed on BART amplification detection instrument at 60° C. The peak times for the faecal sample extracted by IM SDVB-MES-DTT heat lysis followed by PVPP column purification was 50.44±7.59 min. This compared to 43.46±0.76 min for 1 µl from the previously Boom method extracted sample. This showed that Noroviral RNA could be extracted with a method that would be compatible with Heat-Elution.

Example 8: Concentration of Nucleic Acid from the Second Vessel Post Heat-Elution i) Post-Heat Elution, Nucleic Acids can be Further Concentrated.

For low copy number applications, it was demonstrated that concentration of genomic *C. difficile* DNA levels were possible when spiked into reaction buffer i.e. the same reagent composition as the eluate.

Dilutions of *C. difficile* genomic DNA were prepared to $10^3$, $10^2$, 10 and 0 copies per 20 µl in reaction buffer. 20 µl of each dilution was used to reconstitute freeze dried *C. difficile* LAMP-BART reaction mixes in duplicate and run at 60° C.

Each dilution was also concentrated by taking 800 µl of the spikes and mixing with 5 µl of ChargeSwitch® magnetic beads and 160 µl of the kit binding buffer (Invitrogen) for 1 min. The supernatant was removed by settling the beads on a magnetic rack. The beads were re suspended in 80 µl of reaction buffer and 20 µl of the crude suspension, including beads were used to reconstitute freeze dried *C. difficile* LAMP-BART reaction mixes in duplicate and run at 60° C.

FIG. 14 shows that concentration improved detection times of the $10^3$ and $10^2$ copies/20 µl levels by 3.2 to 4.8 min, and permitted reproducibly in detection of both replicates at the 10 copies/20 µl level before 52.3 min, where only 1 of 2 replicates were detected without concentration.

ii) Concentration of *C. difficile* from Positive Faeces with a Simplified ChargeSwitch® Magnetic Bead Method Post Heat-Elution

*C. difficile* positive stool (1 in 5 in reaction buffer) was diluted 1 in 10 with a negative stool (prepared 1 in 5 in reaction buffer). 150 µl (30 mg stool) of the dilution was applied to an 8 ml column (Pierce #89897) containing a particular resin mixture (10% v/v Chelex 100, 25% v/v Optipore SD-2 and 25% v/v Diaion WA30) in BART-LAMP reaction buffer and mixed by hand. The excluded buffer volume was 1.965 ml. The cap was closed tightly and the twist tab was broken off. The column was placed into a 13.5 mm internal diameter collection tube (Fisher #FB51579) and the entire column and tube was placed onto a bespoke heating block. This was heated at 100° C. for 10 min. 20 µl of the collected eluate was used to reconstitute freeze dried *C. difficile* LAMP-BART reactions in duplicate.

800 µl of the eluate was also concentrated by mixing with 5 µl of ChargeSwitch® magnetic beads and 160 µl of the kit binding buffer (Invitrogen) for 1 min. The supernatant was removed by settling the beads on a magnetic rack. The beads were resuspended in 80 µl of reaction buffer and 20 µl of the crude suspension, including beads were used to reconstitute freeze dried *C. difficile* LAMP-BART reaction mixes in duplicate.

The LAMP-BART reactions were run at 60° C. on the BART detection instrument. Concentration of the eluate improved detection time from 27.2±0.5 min (un-concentrated) to 19.2±0 min (post concentration).

iii) Comparison of *C difficile* Genomic DNA Detection with and without Performing Heat-Elution with ChargeSwitch® Magnetic Beads Incorporated into the First Container.

20 µl of *C. difficile* genomic DNA (103 copies per 200 stock was added to 1.98 ml of Bicine buffer. 200 µl of this was used to make serial dilutions with 1.8 ml BICINE buffer at 102 and 101 copies per 20 µl. The gDNA dilutions were treated as follows:

Set 1: No treatment. 20 µl was used to directly reconstitute *C difficile* LAMP BART assays.

Set 2: 400 µl of *C. difficile* gDNA dilution was added to a 1.5 ml Heat-Elution column with a 2.7 mm frit with additional glass filter (G/FD FD #1823-025 paper, Whatman) with 5 µl Charge Switch beads and 80 µl of binding buffer. This was mixed by pipetting. The column lid was secured tightly and placed on the heating block (with a 2 ml collection tube) at 100° C. for 6 min. After elution, the GF/D material with the captured beads was transferred directly to 40 µl of reconstituted *C difficile* LAMP BART assay The conditions with Heat-Elution and magnetic bead concentration helped to detect 1 log lower in dilution series as compared to no Heat-Elution, so demonstrating that Heat-Elution can be used in conjunction with bead-capture methods to concentrate nucleic acids in the Heat-Elution container (FIG. 16).

Example 9: Integration of Multi-Container Sample Preparation & Amplification Using Heat-Elution The principle of heat-elution can be applied such as to combine two or more associated containers which each perform a different function for sample preparation. A single heating block could be used to house such an association of containers, or a number of heating blocks could be used where the timing and rate of heating and final temperature of the heating block is designed to drive the sample in a coherent fashion through the containers.

Further, one vessel could contain NAAT reagents such that the combination of containers and the vessel allows for direct addition of processed sample to NAAT reagents. As such, but appropriate design of heating blocks, once sample is added to the first container, the Heat-Elution method could perform all the steps of sample preparation and allow for adding sample to NAAT reagents and further allowing amplification to proceed (FIG. 15).

Example 10: Heat-Elution can Provide Samples for PCR

Use of Lysate in PCR Detection

An 8 ml column (Pierce #89897) was filled with a proprietary resin mixture in reaction buffer to a final volume of 3.4 ml where the excluded buffer volume was 1.965 ml. A *C. difficile* faecal sample was sampled using a sterile micro ultrafine flocked swab (Puritan #25-3318 1PN 50). The end of the swab was mixed within the resin mixture, the stem of the swab snapped off and the column tightly closed. The column was hand mixed and was placed onto a bespoke heating block that has an insert depth of 80 mm. This was heated at 100° C. for 10 min. The column was allowed to cool and lysate then removed from the top of the column. A *C. difficile* real time PCR reaction mix was prepared using the IQ Supermix (Bio-Rad #170 8862). 4.5 µl of lysate was added to the PCR reactions in duplicate and ran on the ABI-PRISM 7000 together with a *C. difficile* genomic DNA dilution series and amplified following an initial denaturation step at 95° C. for 3 min by 50 cycles 94° C., 57° C. and 72° C. with each at 30 seconds. The lysate gave a Ct value of 29, which corresponded to a copy number of $1.18 \times 10^4$ when calculated from the calibration curve, indicating that the column lysate can also be used for real time PCR detection.

The invention claimed is:

1. A method for passing a liquid sample through a porous solid matrix, comprising the steps of sealing the liquid sample within a container which comprises a porous solid matrix as at least a part of the container and raising a temperature to increase pressure inside the container, thereby to cause the liquid sample to pass through the porous solid matrix, wherein the liquid sample includes a biological sample and a buffer.

2. The method of claim 1, wherein the container comprises two or more different solid porous matrices.

3. The method of claim 1, wherein the liquid sample comprises nucleic acids and inhibitors of nucleic acid amplification.

4. The method of claim 3, wherein the container comprises a porous solid matrix which binds nucleic acids more strongly than inhibitors of nucleic acid amplification.

5. The method of claim 3, wherein the container comprises a porous solid matrix which binds inhibitors of nucleic acid amplification more strongly than nucleic acids.

6. A method for purifying nucleic acids from a liquid sample which comprises nucleic acids and inhibitors of nucleic acid amplification, wherein the method comprises the steps of (a) contacting the liquid sample with a porous solid matrix which binds inhibitors of nucleic acid amplification more strongly than nucleic acids, wherein heat is applied to the porous solid matrix and the liquid sample; and (b) separating the liquid sample comprising unbound nucleic acids from the porous solid matrix, wherein the liquid sample is passed through the porous solid matrix by sealing the liquid sample within a container comprising the porous solid matrix and the heat that is applied raises a temperature to increase pressure inside the container, thereby to cause the liquid to pass through the porous solid matrix, and the liquid sample includes a buffer.

7. The method of claim 6, wherein heat is applied to the liquid sample in step (b).

8. The method of claim 1, wherein the container comprises a flow restrictor which is configured to reduce flow of liquid sample from the container through the porous solid matrix compared to a container which does not have the flow restrictor.

9. The method of claim 8, wherein the flow restrictor is a filter, a frit, or a valve.

10. The method of claim 8, wherein the flow restrictor is a layer of material which melts at a temperature between 45° C. and 110° C.

11. The method of claim 10 wherein the layer of material is a wax.

12. The method of claim 1, further comprising a step of lysing the sample.

13. An apparatus for purifying nucleic acids according to claim 3, comprising
   a) the container comprising the porous solid matrix as at least a part of the container and means for sealing the container, the matrix being capable of binding inhibitors of nucleic acid amplification more strongly than nucleic acids, and
   b) a heating element configured to heat the container to a temperature of up to 110° C.;
   wherein the apparatus is configured to pass liquid through the porous solid matrix by heat.

14. The apparatus of claim 13, wherein the apparatus further comprises a second container to receive liquid passed through the porous solid matrix.

15. The apparatus of claim 13, wherein the apparatus further comprises a vessel comprising reagents for nucleic acid amplification.

16. An apparatus for purifying nucleic acids according to claim 6, comprising
   a) a container comprising a porous solid matrix as at least a part of the container and means for sealing the container, the matrix being capable of binding inhibitors of nucleic acid amplification more strongly than nucleic acids, and
   b) a heating element configured to heat the container to a temperature of up to 110° C.;
   wherein the apparatus is configured to pass liquid through the porous solid matrix by heat.

17. The apparatus of claim 16, wherein the apparatus further comprises a second container to receive liquid passed through the porous solid matrix.

18. The apparatus of claim 16, wherein the apparatus further comprises a vessel comprising reagents for nucleic acid amplification.

* * * * *